US011844790B2

United States Patent
Li et al.

(10) Patent No.: US 11,844,790 B2
(45) Date of Patent: Dec. 19, 2023

(54) METHODS OF TREATING HIDRADENITIS SUPPURATIVA

(71) Applicant: CHEMOCENTRYX, INC., San Carlos, CA (US)

(72) Inventors: Shijie Li, Los Altos, CA (US); Rajinder Singh, Belmont, CA (US); Thomas J. Schall, San Carlos, CA (US); Peter Staehr, San Carlos, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

(21) Appl. No.: 17/512,335

(22) Filed: Oct. 27, 2021

(65) Prior Publication Data

US 2022/0125775 A1 Apr. 28, 2022

Related U.S. Application Data

(60) Provisional application No. 63/106,557, filed on Oct. 28, 2020, provisional application No. 63/106,858, filed on Oct. 28, 2020.

(51) Int. Cl.
*A61K 31/451* (2006.01)
*A61P 17/00* (2006.01)

(52) U.S. Cl.
CPC ............ *A61K 31/451* (2013.01); *A61P 17/00* (2018.01)

(58) Field of Classification Search
CPC .............................. A61K 31/451; A61P 17/00
See application file for complete search history.

(56) References Cited

U.S. PATENT DOCUMENTS

| | | |
|---|---|---|
| 8,445,515 B2 | 5/2013 | Fan et al. |
| 8,906,938 B2 | 12/2014 | Fan et al. |
| 9,126,939 B2 | 9/2015 | Fan et al. |
| 9,290,736 B2 | 3/2016 | Medof et al. |
| 9,573,897 B2 | 2/2017 | Fan et al. |
| 10,035,768 B2 | 7/2018 | Fan et al. |
| 10,329,314 B2 | 6/2019 | Fan et al. |
| 10,376,595 B2 | 8/2019 | Guo et al. |
| 10,487,098 B2 | 11/2019 | Fan et al. |
| 10,562,896 B2 | 2/2020 | Fan et al. |
| 10,683,294 B2 | 6/2020 | Fan et al. |
| 10,759,807 B2 | 9/2020 | Fan et al. |
| 10,828,285 B2 | 11/2020 | Fan et al. |
| 11,026,935 B2 | 6/2021 | Singh et al. |
| 11,254,695 B2 | 2/2022 | Fan et al. |
| 2018/0282425 A1* | 10/2018 | Guo .................... C07K 16/2896 |
| 2019/0062275 A1 | 2/2019 | Fan et al. |
| 2020/0061202 A1 | 2/2020 | Guo et al. |

OTHER PUBLICATIONS

International Search Report and Written Opinion dated Feb. 1, 2022 corresponding to PCT/US2021/056869 filed Oct. 27, 2021; 8 pages.
Press Release: Jul. 2019—InflaRx Reports Additional Analysis of the SHINE Phase IIb Results for IFX-1 in Hidradenitis Suppurativa, https://www.inflarx.de/Home/Investors/Press-Releases/07-2019-InflaRx-Reports-Additional-Analysis-of-the-SHINE-Phase-IIb-Results-for-IFX-1-in-Hidradenitis-Suppurative-.html) (Jul. 18, 2019); 9 pages.
Bekker, Pirow et al., "Characterization of pharmacologic and pharmacokinetic properties of CCX168, a potent and selective orally administered complement 5a receptor inhibitor, based on preclinical evaluation and randomized Phase 1 clinical study." *PloS One* (Oct. 21, 2016) 11(10): e0164646; 19 pages.
Blok, J. L. et al., "Gene expression profiling of skin and blood in hidradenitis suppurativa," *British Journal of Dermatology* (Mar. 2, 2016), 174(6):1392-1394.
Byrd, Angel S. et al., "Neutrophil extracellular traps, B cells, and type I interferons contribute to immune dysregulation in hidradenitis suppurativa," *Sci. Transl. Med.* (Sep. 4, 2019) 11, eaav5908; 12 pages.
Deckers, I. E. et al., "Hidradenitis suppurativa: a pilot study to determine the capability of patients to self-assess their Hurley stage," *British Journal of Dermatology* (Mar. 15, 2015); 172:1418-1419.
Delany, E., et al., "A cross-sectional epidemiological study of hidradenitis suppurativa in an Irish population (SHIP)," *J Eur Acad Dermatol Venereol.* (2018; accepted Oct. 20, 2017); 32:467-473.
Flood, Kelsey S., et al., "Biologic treatment for Hidradenitis suppurativa," *American Journal of Clinical Dermatology* (Published online May 28, 2019); 20:625-638.
Garg, Amit, M.D. et al., "Sex- and Age-Adjusted Population Analysis of Prevalence Estimates for Hidradenitis Suppurativa in the United States," *JAMA Dermatol.* (Published online May 10, 2017);153(8):760-764.

(Continued)

*Primary Examiner* — Timothy R Rozof
(74) *Attorney, Agent, or Firm* — Mintz Levin Cohn Ferris Glovsky and Popeo PC

(57) ABSTRACT

Provided herein are methods for treating a subject suffering from a cutaneous neutrophilic inflammatory disease comprising administering to a subject in need thereof a therapeutically effective amount of a compound of Formula I (I)

or a pharmaceutically acceptable salt thereof, wherein each variable position is as defined herein. In some embodiments, the cutaneous neutrophilic inflammatory disease is Hidradenitis suppurativa (HS).

8 Claims, 1 Drawing Sheet

(56) References Cited

OTHER PUBLICATIONS

Giang, Jenny et al., "Complement Activation in inflammatory Skin Diseases," *Frontiers in Immunology* (Apr. 16, 2018); vol. 9, Article 639; 17 pages.

Goldburg, Samantha R. et al., "Part I. Hidradenitis Suppurativa: Epidemiology, clinical presentation, and pathogenesis," *J Am Acad Dermatol* (2020; Date of Release May 2020) 82(5):1045-1058.

Grand, David et al., "Integrating complement into the molecular pathogenesis of Hidradenitis Suppurativa," *Experimental Dermatology* (2020; Accepted Nov. 1, 2019); 29:86-92.

Guet-Revillet, Helene et al., "The Microbiological Landscape of Anaerobic Infections in Hidradenitis Suppurativa: A Prospective Metagenomic Study," *Clin Infect Dis* (Jul. 15, 2017) 65: 282-291.

Guo, Renfeng et al., "IFX-1 blocking the anaphylatoxin C5a—an anti-inflammatory effect in patients with hidradenitis suppurativa," InflaRx GmbH, Jena, Germany et al. (2017); 1 page.

Hoffman, Lauren K. et al., "Integrating the skin and blood transcriptomes and serum proteome in hidradenitis suppurativa reveals complement dysregulation and plasma cell signature," *PloS One* (Sep. 28, 2018) 13(9): e0203672; 16 pages.

Ingram, J. et al., "Hidradentitis suppurativa: Pathogenesis, clinical features and diagnosis." *UpToDate®* (Version Jul. 2023; topic last updated Dec. 21, 2022); 18 pages.

Investigators Brochure for Avacopan (CCX168), "A Randomized, Double-Blind, Placebo-Controlled Phase 2 Study to Evaluate the Safety and Efficacy of Avacopan (CCX168) in Patients with C3 Glomerulopathy," Edition 9.0 (dated Sep. 25, 2019); 100 pages.

Kanni, T. et al., "Complement activation in hidradenitis suppurativa: a new pathway of pathogenesis?" *British Journal of Dermatology* (May 10, 2018); 179:251-252.

Kidacki, M. et al., "Invasive proliferative gelatinous mass of hidradenitis suppurativa contains distinct inflammatory components," *British Journal of Dermatology* (Dec. 30, 2019) 181:192-193.

Li, Chris et al., "Complement activation and C5aR elevation in Hidradenitis suppurativa patient lesions," Presented at Annual Symposium on Hidradenitis suppurativa advances. (Copyright 2020, ChemoCentryx, Inc.); 7 pages.

Lim, Shi Yu Derek, et al., "Management of severe hidradenitis suppurativa with biologic therapy and wide excision," *Arch Plast Surg* (2019; Accepted Oct. 30, 2018);46:272-276.

Martinelli, Sibylla et al., "Induction of Genes Mediating Interferon-dependent Extracellular Trap Formation during Neutrophil Differentiation," *J. Biol Chem.* (Oct. 15, 2004); 279(42):44123-44132.

Olsen, Ingar et al., "Porphyromonas gingivalis disturbs host-commensal homeostasis by changing complement function," *Journal of Oral Microbiology* (Published online Jun. 30, 2017) 9:1340085; 12 pages.

Saunte, Ditte Marie Lindhardt, M.D., Ph.D., et al. "Hidradenitis suppurativa: advances in diagnosis and treatment," *JAMA* (Nov. 28, 2017); 318(20):2019-32.

Savage, Kevin T. et al., "TNFα inhibitors in the treatment of hidradenitis suppurativa," *Ther Adv Chronic Dis* (2019; revised manuscript accepted Apr. 18, 2019); 10: 1-12.

Savage, Kevin T. et al., "Methotrexate shows benefit in a subset of patients with severe hidradenitis suppurativa," International Journal of Women's Dermatology (2020; Accepted Feb. 19, 2020); 6 :59-163.

Schrader, Anne M. R., M.D. et al., "Hidradenitis suppurativa: a retrospective study of 846 Dutch patients to identify factors associated with disease severity," *J Am Acad Dermatol* (Accepted for publication Apr. 1, 2014); 71:460-467.

Unnewehr, Heike et al., "Changes and regulation of the C5a receptor on neutrophils during septic shock in humans," *J Immunol* (Apr. 15, 2013); 190(8):4215-4225.

Vanlaerhoven, Annika, M.J.D. et al., "Hurley III Hidradenitis Suppurativa Has an Aggressive Disease Course," *Dermatology* (Published online Aug. 27, 2018); 234:232-233.

Van Der Zee, H. H. et al., "Can Animal Skin Diseases or Current Transgenic Mice Serve as a Model for Hidradenitis Suppurativa?" *Dermatology* (Published online Aug. 14, 2012); 225:9-13.

Vazquez, Benjamin G. et al., "Incidence of hidradenitis suppurativa and associated factors: a population-based study of Olmsted County, Minnesota," *J Invest Dermatol* (2013; Published online Aug. 30, 2012); 133(1):97-103.

Vossen, Allard R. J. V. et al., "Hidradenitis Suppurativa: A Systematic Review Integrating Inflammatory Pathways Into a Cohesive Pathogenic Model," *Front. Immunol.* (Dec. 14, 2018); 9:2965; 12 pages.

\* cited by examiner

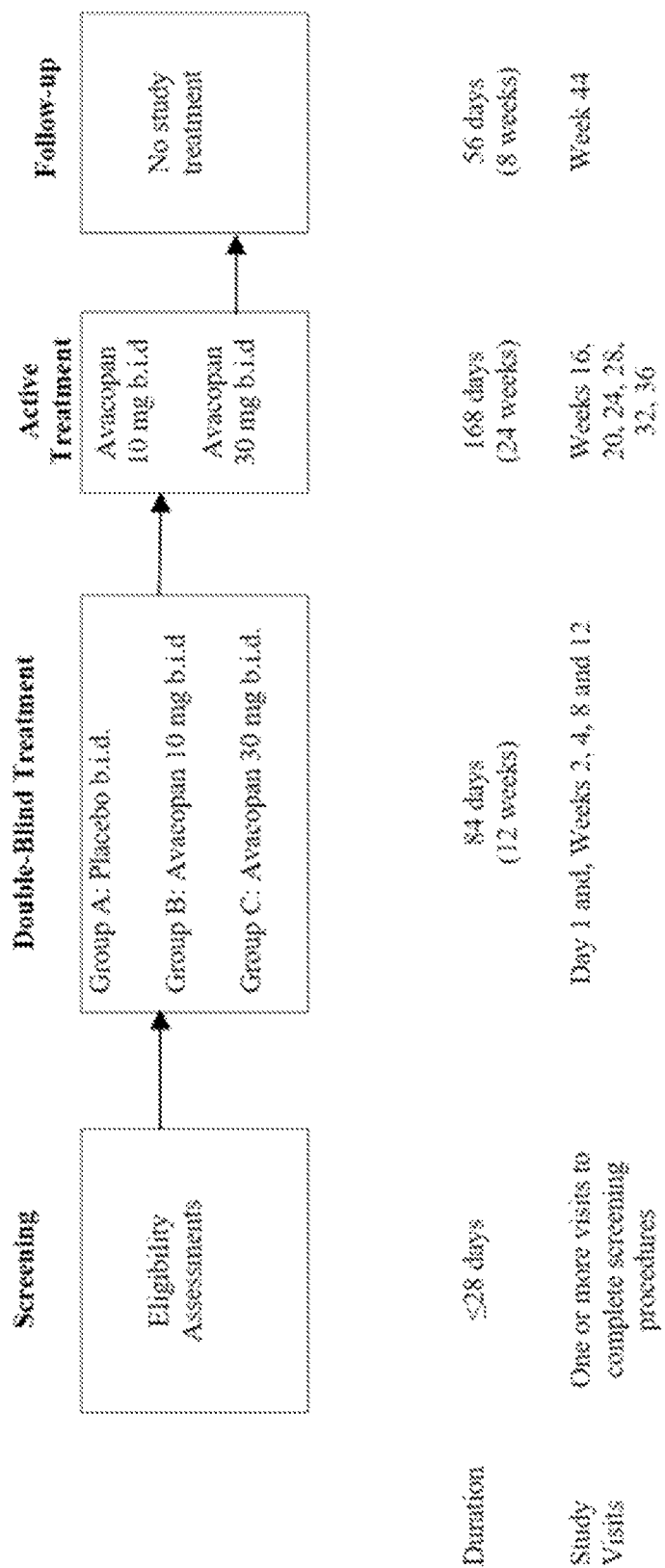

METHODS OF TREATING HIDRADENITIS SUPPURATIVA

CROSS-REFERENCES TO RELATED APPLICATIONS

This application claims the benefit of priority under 35 U.S.C. § 119(e) to U.S. Provisional Application Ser. No. 63/106,557 filed Oct. 28, 2020 and U.S. Provisional Application Ser. No. 63/106,858 filed Oct. 28, 2020, the contents of each is herein incorporated by reference in their entirety for all purposes.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

Hidradenitis suppurativa (HS), also called acne inversa, is a chronic inflammatory skin disease characterized by inflammatory nodule, abscess, sinus and fistula formation, and scarring of the skin, most commonly in apocrine gland rich areas such as the axilla, inframammary area, inguinal area, perineum, and perianal area. In its moderate and severe forms, HS is debilitating and causes significant discomfort, pain, anxiety and depression, as well as impairment of quality of life.

The exact cause of HS has not been identified, although genetic defects in the gene encoding for gamma-secretase have been described in subjects with HS. Potential target proteins include Notch, E-cadherin, and nicastrin. Notch plays an important role in hair follicle development, and a defect in Notch may lead to formation of epidermal cysts, dysregulation of normal T-cell mediated immune responses, and suppression of Toll-like receptor-4-induced pro-inflammatory macrophage mediated cytokine responses (Radtke et al, 2010; Wang et al, 2010). Smoking and obesity have been associated with HS (Prens and Deckers, 2015) as well as, excessive sweating, androgen dysfunction, or possible genetic causes. Some reports suggest that HS is, at least in part, a neutrophil mediated disease.

Current therapy for subjects with HS includes local and systemic antibiotics, pain medication, and anti-TNF-α agents such as adalimumab. Other drugs such as cyclosporin A, dapsone, and isotretinoin have been used with limited success (Napolitano et al, 2017). Despite the treatment options available, most patients only partially and/or temporarily respond.

A recent treatment option advanced in US2018/0280530 and US2018/028425 is the use of a C5a targeting antibody to treat patients suffering from HS. C5a is known to be a potent chemotactic anaphylatoxin, and the binding of C5a to C5aR modulates leucocyte trafficking, migration, and activation. However, targeting C5a directly with an antibody disrupts not only the C5a/C5aR axis, but also disrupts C5a binding to the C5L2 receptor. The C5a/C5L2 pathway includes beneficial biological functions including limiting or suppressing the pro-inflammatory response caused by C5a (Gerard et al. J Biol Chem. 2005. 280(48):39677-80, Wang et al. J Immunol. 2013. 191(8):4001-9). In fact, disrupting the C5a-C5L2 pathway has been shown to exacerbate inflammation resulting in a more severe reaction to C5a. (Xiao et al. J Am Soc Nephrol. 2014. 25(2):225-31, Karsten et al., Front Immunol. 2018, 15; 9:488). Thus, the direct targeting of C5a involves blocking signaling pathways associated with mitigating C5a response.

Moreover, antibody treatments carry other disadvantages such as the need for intravenous delivery, the potential for patients to develop human anti-chimeric antibodies (HACAs), the need for patients to travel to a medical center to receive treatment, and reduced patient compliance.

As such, there remains a need in the art to identify and develop orally available compounds useful in the treatment of Hidradenitis Suppurativa (HS) and related cutaneous neutrophilic inflammatory diseases that do not block the C5a/C5L2 axis, thereby preserving the beneficial functions of the C5L2 pathway.

BRIEF SUMMARY OF THE INVENTION

In one aspect, the present disclosure provides methods treating a cutaneous neutrophilic inflammatory disease in a subject in need thereof, said method comprising administering to said subject a therapeutically effective amount of a compound of Formula I

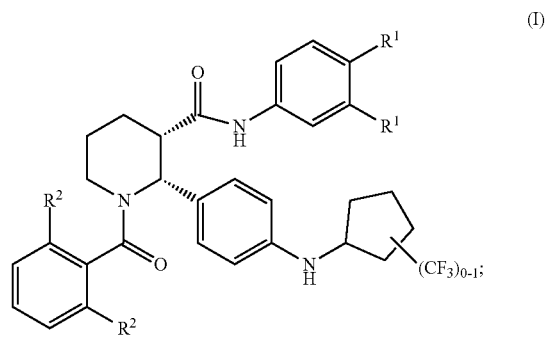

or a pharmaceutically acceptable salt thereof, wherein $R^1$ and $R^2$ are as defined herein.

In some embodiments, the cutaneous neutrophilic inflammatory disease is Hidradenitis Suppurativa (HS).

In some embodiments, the therapeutically effective amount of Formula I is a total daily dosage of about 5 to 200 mg. In some embodiments, the therapeutically effective amount of Formula I is a total daily dosage of 60 mg or 20 mg.

Other objects, features, and advantages of the present invention will be apparent to one of skill in the art from the following detailed description and FIGURES.

BRIEF DESCRIPTION OF THE DRAWINGS

FIG. 1 shows a schematic of the Phase II study design.

DETAILED DESCRIPTION OF THE INVENTION

I. General

The current disclosure provides compounds and dosing regimens for the treatment of Hidradenitis Suppurativa and specific patient populations thereof. The compounds in the methods described herein specifically target C5aR and do not disrupt the C5a-C5L2 interaction. Advantageously, the C5aR inhibitors disclosed in this application effectively modulate neutrophil migration and activation by blocking the C5a-C5aR interaction while not blocking the C5a-C5L2 axis. Without being bound to any particular theory, it is believed that compounds binding to C5aR avoid the detrimental effects of interrupting the C5a-C5L2 signaling axis. This provides subjects receiving treatment for Hidradenitis Suppurativa and subpopulations thereof to benefit from the pro-inflammatory suppressing activity of the C5a-C5L2 axis.

II. Definitions

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). Treatment methods provided herein include, in general, administration to a patient an effective amount of one or more compounds provided herein. Suitable patients include those patients suffering from or susceptible to {i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, a wavy line, "∿", that intersects a single, double or triple bond in any chemical structure depicted herein, represent the point attachment of the single, double, or triple bond to the remainder of the molecule.

III. Detailed Description of Embodiments

A. Methods of Treatment

In one aspect, the present disclosure provides methods of treating a cutaneous neutrophilic inflammatory disease in a subject in need thereof, said method comprising administering to said subject a therapeutically effective amount of a compound of Formula I,

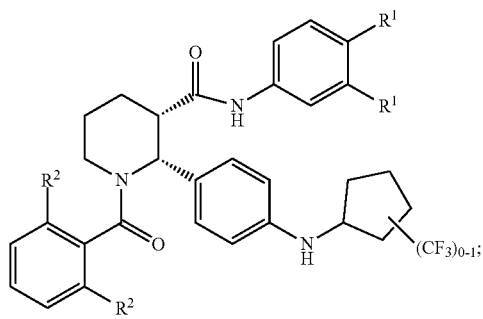

or a pharmaceutically acceptable salt thereof, wherein
each $R^1$ is independently selected from the group consisting of $CH_3$, $CF_3$, $CH_2CH_3$, Cl, 1-pyrrolidine, —O—CH($CH_3$)$_2$, and $CH_2OH$; and
each $R^2$ is independently selected from the group consisting of $CH_3$ and F.

Cutaneous neutrophilic inflammatory diseases are a class of diseases that are driven, at least in part, by the over activity or inappropriate activation of neutrophils. The methods provided herein are particularly useful in treating Hidradenitis Suppurativa (HS), a disease that is mediated, at least in part, by neutrophil activity. The treatment methods contemplated in this disclosure, however, are not limited to HS, and further include related cutaneous neutrophilic inflammatory diseases such as Sweet syndrome (SS), Pyoderma gangrenosum (PG), PAPA (pyogenic arthritis, PG and acne), PASH (PG, acne and hidradenitis suppurativa), subcorneal pustular, dermatosis (SPD), PAPASH (pyogenic arthritis, acne, PG and hidradenitis suppurativa), elevatum diutinum (EED), neutrophilic panniculitis, epidermolysis bullosa acquisita, syndrome; rheumatoid neutrophilic dermatosis, familial Mediterranean fever, erythema, Schnitzler syndrome, bowel-associated dermatosis-arthritis syndrome (BADAS), SAPHO (synovitis, acne, pustulosis, hyperostosis, and osteitis) cryopyrin-associated disorders, and gout.

In some embodiments, the compounds of Formula I are used to treat Hidradenitis Suppurativa (HS).

Certain subpopulations of subjects can respond surprisingly well to treatment with compounds of Formula I. For example, in some embodiments, women responded significantly better to treatment as compared to men. In some embodiments, younger subjects (e.g. 50 years or younger) responded significantly better to treatment as compared to elderly subjects (e.g., 51 years of age or older). In some embodiments, subjects diagnosed with Hurley Stage III Hidradenitis Suppurativa responded significantly better than subject with less severe forms. In some embodiments, subjects who had previously received an anti-TNF-α drug (e.g., adalimumab or infliximab responded surprisingly better as compared to those who had not previously received an anti-TNF-α drug. In some embodiments, subjects who were concomitantly treated with antibiotic therapy (e.g., doxycycline or minocycline) responded surprisingly better as compared to subjects with no concomitant antibiotic therapy. In each of the above embodiments, still other embodiments are those wherein Avacopan is administered as the compound of Formula I, either at a dose of 10 mg bid, or at 30 mg bid.

In some embodiments, subjects diagnosed with Hurley Stage III Hidradenitis Suppurativa responded significantly better than subjects with less severe forms. In some embodiments, subjects who had previously received an anti-TNF-α drug (e.g., adalimumab or infliximab responded surprisingly better as compared to those who had not previously received an anti-TNF-α drug. In each of these embodiments, treatment is effective when Avacopan is administered in an amount of 30 mg bid.

When comparing patient subpopulations, a variety of clinically defined metrics can be used. For example, significant improvements can be observed by measuring one of more of the following metrics: abscess and inflammatory nodule (AN) count, a subject's global assessment of skin pain (NRS), proportion of subjects with a flare during treatment, proportion of subjects who received oral antibiotic rescue therapy or intralesional Kenalog® rescue injection, change in modified Sartorius score, change in IHS4 score, change in hidradenitis suppurativa Physician Global Assessment (HS-PGA), change in Hidradenitis Suppurativa Burden of Disease (HSBOD) score, change in Cardiff Dermatology Life Quality Index or DLQI questionnaire, change in Work Productivity and Activity Impairment Questionnaire: Specific Health Problem (WPAI:SHP) achieving a Hidradenitis Suppurativa Clinical Response (HiSCR) (HiSCR is defined as at least a 50% reduction in abscess and inflammatory nodule (AN) count and no increase in abscess count and no increase in draining fistula count), etc.

As measured by abscess and inflammatory nodule (AN) count, populations of subjects who respond significantly better to treatment include those where the proportion of the population that achieves a reduction in AN count is at least 5, 10, 15, 20, or 25% or more than the proportion of subjects who are not in the defined population.

As measured by global assessment of skin pain (NRS), populations of subjects who respond significantly better to treatment include those where the proportion of subjects achieving at least 30% reduction in the subject's global assessment of skin pain (NRS) is at least 5, 10, 15, 20, or 25% or more than the proportion of subjects who are not in the defined population. For the analysis of NRS30, weekly averages of the worst skin pain recorded by subjects for each 24-hour period in daily diaries will be calculated for each of the relevant study visits.

As measured by proportion of subjects with a flare during treatment, populations of subjects who respond significantly better to treatment include those where the proportion of the population that does not experience a flare while under going treatment is at least 5, 10, 15, 20, or 25% or more than the proportion of subjects who are not in the defined population.

As measured by proportion of subjects who received oral antibiotic rescue therapy or intralesional Kenalog® rescue injection, populations of subjects who respond significantly better to treatment include those where the proportion of the population that does not receive oral antibiotic rescue therapy while under going treatment is at least 5, 10, 15, 20, or 25% or more than the proportion of subjects who are not in the defined population.

As measured by change in modified Sartorius score, populations of subjects who respond significantly better to treatment include those where the proportion of subjects achieving at least a 4 or 5 point reduction in the subject's modified Sartorius score is at least 5, 10, 15, 20, or 25% or more than the proportion of subjects who are not in the defined population.

As measured by change in IHS4 score, populations of subjects who respond significantly better to treatment include those where the proportion of subjects achieving at least a 4 or 5 point reduction in the subject's IHS4 score is at least 5, 10, 15, 20, or 25% or more than the proportion of subjects who are not in the defined population. In some embodiments, subjects with Hurley Stage III Hidradenitis Suppurativa respond significantly better to treatment as compared to subjects not having Hurley Stage III Hidradenitis Suppurativa. In some embodiments, the proportion of subjects with Hurley Stage III Hidradenitis Suppurativa achieving at least a 4 or 5 point reduction in the subject's IHS4 score is at least 10% greater than the proportion of subjects not having Hurley Stage III Hidradenitis Suppurativa after 12 weeks of treatment as compared to baseline. In some embodiments, the proportion of subjects with Hurley Stage III Hidradenitis Suppurativa achieving at least a 4 or 5 point reduction in the subject's IHS4 score is at least 15% greater than the proportion of subjects not having Hurley Stage III Hidradenitis Suppurativa after 12 weeks of treatment as compared to baseline. In some embodiments, the proportion of subjects with Hurley Stage III Hidradenitis Suppurativa achieving at least a 4 or 5 point reduction in the subject's IHS4 score is at least 20% greater than the proportion of subjects not having Hurley Stage III Hidradenitis Suppurativa after 12 weeks of treatment as compared to baseline.

As measured by change in HS-PGA score, populations of subjects who respond significantly better to treatment include those where the proportion of subjects achieving at least a 2 or 3 point reduction in the subject's HS-PGA score is at least 5, 10, 15, 20, or 25% or more than the proportion of subjects who are not in the defined population.

As measured by change in HSBOD score, populations of subjects who respond significantly better to treatment include those where the proportion of subjects achieving at least a 2 or 3 point reduction in the subject's HSBOD score is at least 5, 10, 15, 20, or 25% or more than the proportion of subjects who are not in the defined population.

As measured by change in DLQI questionnaire score, populations of subjects who respond significantly better to treatment include those where the proportion of subjects achieving at least a 4 or 5 point reduction in the subject's DLQI questionnaire score is at least 5, 10, 15, 20, or 25% or more than the proportion of subjects who are not in the defined population.

As measured by Work Productivity and Activity Impairment Questionnaire: Specific Health Problem (WPAI:SHP), populations of subjects who respond significantly better to treatment include those where the proportion of subjects achieving at least 15% reduction in the WPAI:SHP is at least 5, 10, 15, 20, or 25% or more than the proportion of subjects who are not in the defined population.

As measured by Hidradenitis Suppurativa Clinical Response (HiSCR), populations of subjects who respond significantly better to treatment include those where the proportion of the population that achieves a HiSCR assessment is at least 5, 10, 15, 20, or 25% or more higher than the population of subjects who are not in the defined population. In some embodiments, subjects with Hurley Stage III Hidradenitis Suppurativa respond significantly better to treatment as compared to subjects not having Hurley Stage III Hidradenitis Suppurativa. In some embodiments, subjects with Hurley Stage III Hidradenitis Suppurativa respond significantly better to treatment as compared to subjects not having Hurley Stage III Hidradenitis Suppurativa. In some embodiments, the proportion of subjects with Hurley Stage III Hidradenitis Suppurativa achieving a HiSCR assessment is at least 10% greater than the proportion of subjects not having Hurley Stage III Hidradenitis Suppurativa after 12 weeks of treatment as compared to baseline. In some embodiments, the proportion of subjects with Hurley Stage III Hidradenitis Suppurativa achieving a HiSCR assessment is at least 15% greater than the proportion of subjects not having Hurley Stage III Hidradenitis Suppurativa after 12 weeks of treatment as compared to baseline. In some embodiments, the proportion of subjects with Hurley Stage III Hidradenitis Suppurativa achieving a HiSCR assessment is at least 20% greater than the proportion of subjects not having Hurley Stage III Hidradenitis Suppurativa after 12 weeks of treatment as compared to baseline.

The observed clinical changes in populations or subpopulations can vary depending on the timeframe for comparison. In some embodiments, the comparison in the preceding paragraphs is the change from Day 1 to Week 2. In some embodiments, the comparison in the preceding paragraphs is the change from Day 1 to Week 4. In some embodiments, the comparison in the preceding paragraphs is the change from Day 1 to Week 8. In some embodiments, the comparison in the preceding paragraphs is the change from Day 1 to Week 12. In some embodiments, the comparison in the preceding paragraphs is the change from Day 1 to Week 16. In some embodiments, the comparison in the preceding paragraphs is the change from Day 1 to Week 20. In some embodiments, the comparison in the preceding paragraphs is the change from Day 1 to Week 24. In some embodiments, the comparison in the preceding paragraphs is the change from Day 1 to Week 28. In some embodiments, the comparison in the preceding paragraphs is the change from Day 1 to Week 32. In some embodiments, the comparison in the preceding paragraphs is the change from Day 1 to Week 36. In some embodiments, the comparison in the preceding paragraphs is the change from Day 1 to Week 44.

The therapeutically effective amount will depend upon a variety of factors including the activity of the specific compound employed, the disease being treated, and, in some embodiments, particular aspects of the individual receiving treatment. In some embodiments, a therapeutically effective amount is a total daily dose of about 5 to 200 mg. In some embodiments, a therapeutically effective amount is a total daily dose of about 10 to 150 mg. In some embodiments, a therapeutically effective amount is a total daily dose of about 15 to 100 mg. In some embodiments, a therapeutically effective amount is a total daily dose of about 20 to 60 mg. In some embodiments, a therapeutically effective amount is a total daily dose of about 60 mg. In some embodiments, a therapeutically effective amount is a total daily dose of about 50 mg. In some embodiments, a therapeutically effective amount is a total daily dose of about 40 mg. In some embodiments, a therapeutically effective amount is a total daily dose of about 30 mg. In some embodiments, a therapeutically effective amount is a total daily dose of about 20 mg.

The therapeutically effective amount can also be expressed as a steady state mean blood plasma concentration. For example, in some embodiments, a therapeutically effective amount of the compound of Formula I achieves and maintains a steady state mean blood plasma concentration of about 50 ng/mL to 400 ng/mL. In some embodiments, a therapeutically effective amount of the compound of Formula I achieves and maintains a steady state mean blood plasma concentration of about 150 ng/mL to 250 ng/mL. In some embodiments, a therapeutically effective amount of the compound of Formula I achieves and maintains a steady state mean blood plasma concentration of about 175 ng/mL to 225 ng/mL. In some embodiments, a therapeutically effective amount of the compound of Formula I achieves and maintains a steady state mean blood plasma concentration of about 50 ng/mL to 90 ng/mL. n some embodiments, a therapeutically effective amount of the compound of Formula I achieves and maintains a steady state mean blood plasma concentration of about 60 ng/mL to 70 ng/mL. In some embodiments, a therapeutically effective amount of the compound of Formula I achieves and maintains a steady state mean blood plasma concentration of about 195 ng/mL. In some embodiments, a therapeutically effective amount of the compound of Formula I achieves and maintains a steady state mean blood plasma concentration of about 205 ng/mL. In some embodiments, a therapeutically effective amount of the compound of Formula I achieves and maintains a steady state mean blood plasma concentration of about 215 ng/mL. In some embodiments, a therapeutically effective amount of the compound of Formula I achieves and maintains a steady state mean blood plasma concentration of about 60 ng/mL. In some embodiments, a therapeutically effective amount of the compound of Formula I achieves and maintains a steady state mean blood plasma concentration of about 65 ng/mL. In some embodiments, a therapeutically effective amount of the compound of Formula I achieves and maintains a steady state mean blood plasma concentration of about 70 ng/mL.

B. Compounds of Formula I

Compounds of Formula (I), or a pharmaceutically acceptable salt thereof, have the structure

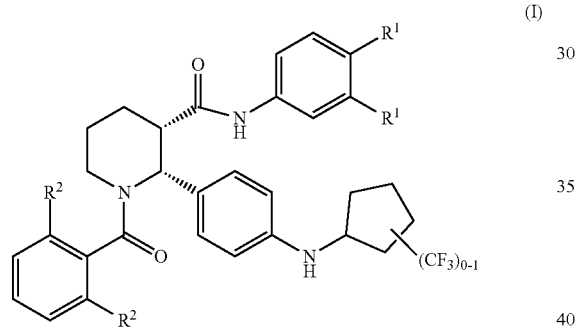

wherein
  each $R^1$ is independently selected from the group consisting of $CH_3$, $CF_3$, $CH_2CH_3$, Cl, 1-pyrrolidine, —O—$CH(CH_3)_2$, and $CH_2OH$; and
  each $R^2$ is independently selected from the group consisting of $CH_3$ and F.

In some embodiments, the compound of Formula I has the formula

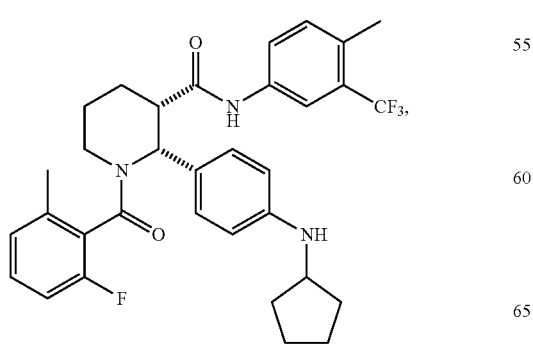

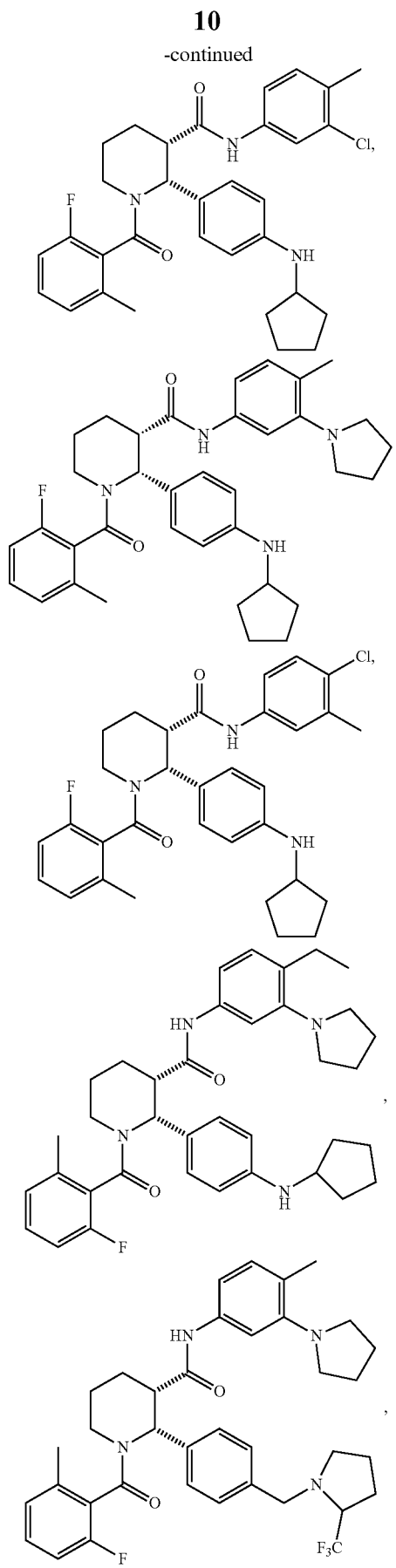

11
-continued
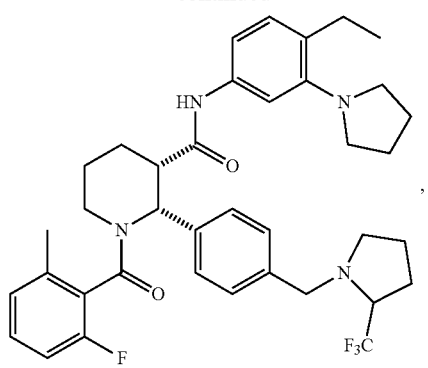,
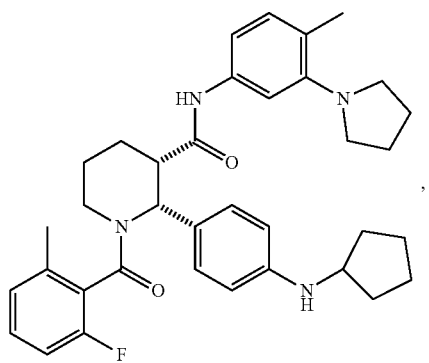,
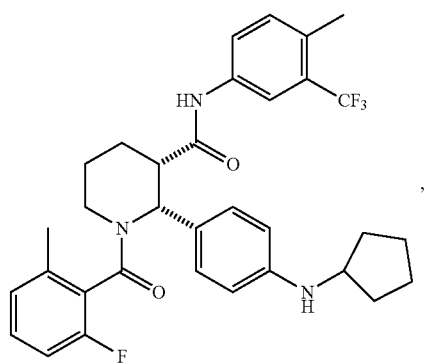,
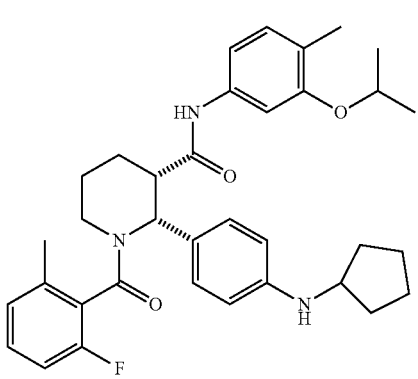,
12
-continued
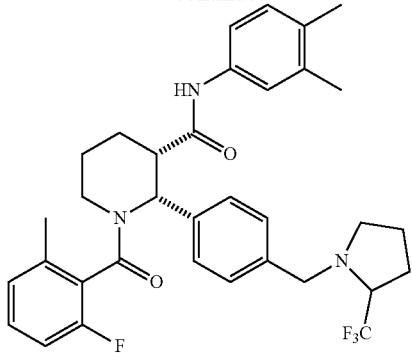,
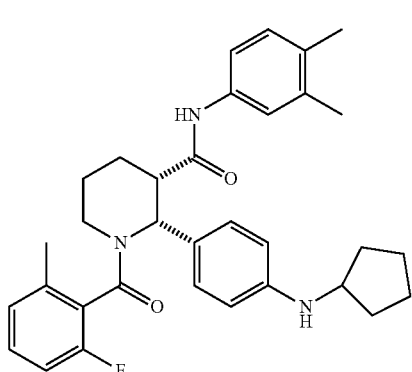,
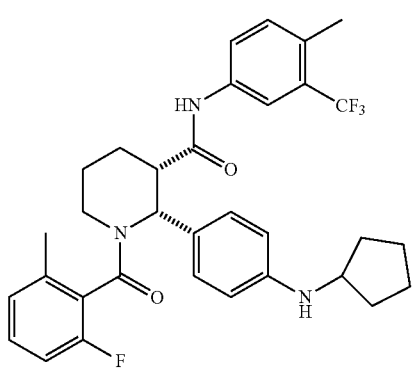,
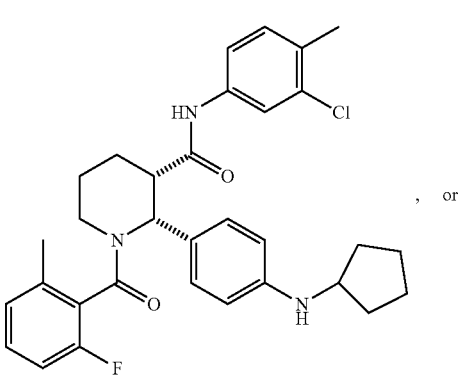, or

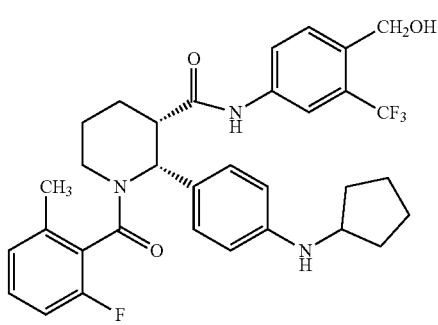 [SMILES: Cc1cccc(F)c1C(=O)N1CCC[C@H](C(=O)Nc2ccc(CO)c(C(F)(F)F)c2)[C@@H]1c1ccc(NC2CCCC2)cc1]

or a pharmaceutically acceptable salt thereof

In some embodiments, the compound of Formula I has the formula

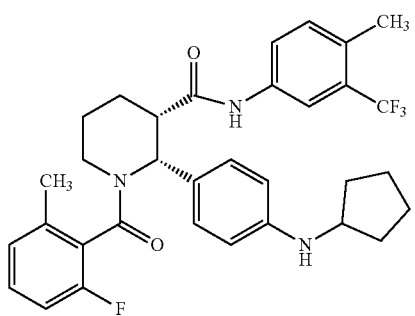 [SMILES: Cc1ccc(NC(=O)[C@H]2CCCN(C(=O)c3c(C)cccc3F)[C@H]2c2ccc(NC3CCCC3)cc2)cc1C(F)(F)F]

or a pharmaceutically acceptable salt thereof.

In some embodiments, the compound of Formula I is Avacopan, having the formula

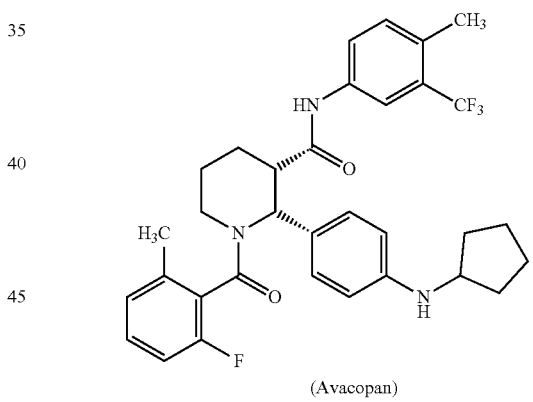

or a pharmaceutically acceptable salt thereof.

The compounds of Formula (I) described herein can be obtained according to methods described in WO 2010/075257, WO 2011/163640 and WO 2016/053890, the contents of each is hereby incorporated by reference for all purposes. In some embodiments, the compound of Formula (I) is a compound described in one of these references.

C. Methods of Administration

In general, treatment methods provided herein comprise administering to a patient an effective amount of a compound in specific dosages and timing to effectively treat hidradenitis suppurative (HS) or a cutaneous neutrophilic inflammatory disorder. In some embodiments, the compound is administered to a subject (e.g., a human) orally. Treatment regimens may vary depending on the compound used and the route of administration, but a frequency of administration of 4 times daily or less is preferred. In some embodiments, a dosage regimen of 2 times daily is used. n some embodiments, a dosage regimen of 1 time daily is used.

The amount of time the individual receives treatment will depend on a variety of factors including the disease being threated as well as the age, body weight, general health, sex, diet, time of administration, and route of administration of the compound. In some embodiments, the subject receives treatment for 12 weeks. In some embodiments, the subject receives treatment for 26 weeks. In some embodiments, the subject receives treatment for 52 weeks. In some embodiments, the subject receives chronic treatment.

In some embodiments, the subject is orally administered 10 mg of Avacopan twice daily, for a total daily dose of 20 mg.

In some embodiments, the subject is orally administered 15 mg of Avacopan twice daily, for a total daily dose of 30 mg.

In some embodiments, the subject is orally administered 20 mg of Avacopan twice daily, for a total daily dose of 40 mg.

In some embodiments, the subject is orally administered 25 mg of Avacopan twice daily, for a total daily dose of 50 mg.

In some embodiments, the subject is orally administered 30 mg of Avacopan twice daily, for a total daily dose of 60 mg.

In some embodiments, the methods described herein used solid solution capsule formulations comprising Avacopan as a free base, in its neutral form or in the form of a pharmaceutically acceptable salt (Avacopan)

and a vehicle comprising
  at least one non-ionic surfactant has a hydrophilic-lipophilic balance (HLB) value of at least 10, and
  at least one water-soluble solubilizer having a melting point at or above 37° C.

Typically, suitable non-ionic surfactants having an HLB value of at least 10 include (a) polyoxyethylene castor oil derivatives, and (b) polyoxyethylene derivatives of polyol esters, wherein the polyoxyethylene derivative of polyol ester is derived from a fatty acid containing from about 8 to about 22 carbon atoms. The carbon atoms of the fatty acid can include one or more points of unsaturation or one or more points of substitution (e.g. ricinoleic acid).

In some embodiments, suitable non-ionic surfactants having an HLB value of at least 10 are macrogol-glycerol hydroxystearate polymers such as polyoxyethylene 40 castor oil, polyoxyethylene 40 hydrogenated castor oil (also known as macrogol-40-glycerol hydroxystearate, it previous tradename Cremophor® RH40, and its current tradename Kolliphor® RH40), macrogolglycerol ricinoleate (also known as polyethoxxethylene 35 castor oil, by its previous tradename Cremophor® EL, and by its current tradename Kolliphor® EL), macrogol-15-hydroxystearate (also known by its previous tradename Solutol® HS 15 and its current tradename Kolliphor HS15), polyoxyethylene 60 castor oil, polyoxyethylene 60 hydrogenator castor oil, polyoxyethylene 100 hydrogenated castor oil, polyoxyethylene 200 castor oil, polyoxyethylene 200 hydrogenated castor oil.

Suitable water-soluble solubilizers having a melting point at or above 37° C. can be polyethylene glycols (PEGs) having a minimum average molecular weight of 1000 and a maximum average molecular weight of 20,000. Typical polyethylene glycols used as solubilizers in the present invention are PEG-1000, PEG-1500, PEG-1540, PEG-2000, PEG-3000, PEG-3350, PEG-4000, PEG-6000, PEG-8000, PEG-10000, and PEG-20000. In some embodiments, the at least one water-soluble solubilizer is PEG-3000, PEG-3350, PEG-4000, PEG-6000. In some embodiments, the at least one water-soluble solubilizer is PEG-4000.

Also suitable as water-soluble solubilizers having a melting point at or above 37° C. are solid poloxamers, also known as poloxamer polyols with average molecular weights between 6000 and 18000 or by their tradename Pluronics®, which have the formula $HO(C_2H_4O)_a(C_3H_6O)_b(C_2H_4O)_aH$. Examples of suitable poloxamers are poloxamer 188, poloxamer 237, poloxamer 338 and poloxamer 407.

In certain embodiments, the at least one non-ionic surfactant having a hydrophilic-liphophilic balance (HLB) value of at least 10 and the at least one water-soluble solubilizer having a melting point at or above 37° C. is a single component. Such a component includes a hydrophilic polyethylene glycol (PEG) chain attached to a lipophilic fatty acid or fatty alcohol component (e.g. a macrogolglycerol hydroxystearate). The longer the PEG chain length, i.e. the higher the HLB value, the more likely it is that dissociation between the PEG chain and the lipophilic component occurs. Such single component vehicles provide a non-ionic surfactant having an HLB value of at least 10 and free PEG polymer chains acting as water-soluble solubilizers.

Without wishing to be bound by any particular theory, it is thought that a capsule formulation comprising a non-ionic surfactant having an HLB value of at least 10 and a water-soluble solubilizer having a melting point at or above 37° C. provides a so-called self-emulsifying or self-solubilizing system. Upon oral administration, the capsule shell dissolves in the gastrointestinal tract followed by dissolution of the solubilizing agent in the gastric fluid with simultaneous formation of micelles comprising molecularly dissolved Avacopan. Thus, a microemulsion or a nanoemulsion is formed that permits Avacopan to remain in solution despite being surrounded by gastric fluid having a pH value of 3 or above, at which pH value Avacopan is normally insoluble.

In some embodiments, the solid solution capsule formulations comprising Avacopan as a free base, in its neutral form or in the form of a pharmaceutically acceptable salt, and a vehicle, said vehicle comprising macrogol-40-glycerol hydroxystearate and PEG-4000.

In some embodiments, the vehicle comprises about 97 to 99% by weight of the total fill weight of said solid solution capsule. In some embodiments, the vehicle comprises about 98% by weight of the total fill weight of said solid solution capsule.

In some embodiments, the solid solution capsule comprises about 1 to 3% of Avacopan by weight of the total fill weight of said solid solution capsule. In some embodiments, the solid solution capsule comprises about 1 to 2.8% of Avacopan by weight of the total fill weight of said solid solution capsule. In some embodiments, the solid solution capsule comprises about 2% of Avacopan by weight of the total fill weight of said solid solution capsule.

In some embodiments, the total weight of the vehicle comprises a 30:70 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 30:70 and 65:35. In some embodiments, the total weight of the vehicle comprises a 35:65 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 35:65 to 65:35. In some embodiments, the total weight of the vehicle comprises a 45:55 to 55:45 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 45:55 to 55:45. In some embodiments, the total weight of the vehicle comprises about a 50:50 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 50:50. In some embodiments, the total weight of the vehicle comprises about a 40:60 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 40:60. In some embodiments, the total weight of the vehicle comprises about a 30:70 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 30:70.

In some embodiments, the total fill weight of said solid solution capsule is about 100 mg to about 1,000 mg. In some embodiments, the total fill weight of said solid solution capsule is about 130 mg to about 900 mg. In some embodiments, the total fill weight of said solid solution capsule is about 250 mg to about 750 mg. In some embodiments, the total fill weight of said solid solution capsule is about 500 mg.

In some embodiments, the solid solution capsule does not include ethanol.

In some embodiments, the solid solution capsule is in a capsule of size #00, #0, #1, #2, #3, #4, or #5. In some embodiments, the solid solution capsule is in a capsule of size #00. In some embodiments, the solid solution capsule is in a capsule of size #0. In some embodiments, the solid solution capsule is in a capsule of size #1.

In some embodiments, the capsule is a hard capsule. In some embodiments, the capsule is a soft capsule.

Capsules of the present disclosure can be sealed using known techniques in the art. For example, a gelatin sealing band comprising a plasticizer such as polysorbate 80 can be used to seal the capsules disclosed herein.

E. Method of Making a Solid Solution Capsule of Formula I

The solid solution capsule formulations described herein are manufactured by filling hard shell capsules with warmed drug solution. After filling the warmed drug solution into the capsules, the solution solidifies and form an amorphous matrix.

In some aspects, provided herein are methods of preparing a solid solution capsule comprising Avacopan as a free base, in its neutral form or in the form of a pharmaceutically acceptable salt

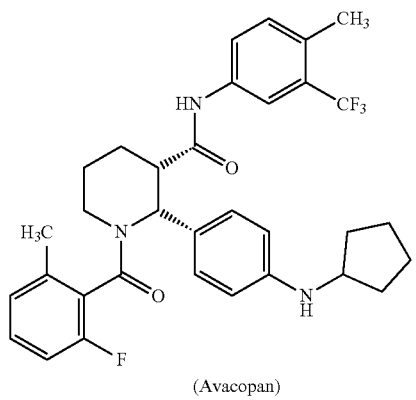

(Avacopan)

and a vehicle comprising
at least one non-ionic surfactant having a hydrophilic-lipophilic balance (HLB) value of at least 10, and
at least one water-soluble solubilizer having a melting point at or above 37° C.; said method comprising
(a) melting the vehicle;
(b) combining the melted vehicle obtained in step (a) with Avacopan to form a drug solution;
(c) encapsulating the drug solution in a capsule shell; and
(d) cooling the encapsulated drug solution to form a solid solution capsule comprising Avacopan.

Melting the vehicle is achieved using standard techniques in the art. The temperature for melting will depend on the identity of the vehicle. Typical melting techniques include direct heating oven and jacketed mixing tanks. In some embodiments, the vehicle in step (a) is heated to about 40, 45, 50, 55, 60, 65, 70, 75, 80, 85, 90 or more degrees C. In some embodiments, the vehicle in step (a) is heated to about 50° to 85° C. In some embodiments, the vehicle in step (a) is heated to about 50° C. In some embodiments, the vehicle in step (a) is heated to about 60° C. In some embodiments, the vehicle in step (a) is heated to about 70° C. In some embodiments, the vehicle in step (a) is heated to about 80° C.

In some embodiments, step (a) comprises
(i) heating at least one non-ionic surfactant having an HLB value of at least 10 to form a melted surfactant;
(ii) heating at least one water-soluble solubilizer to form a melted solubilizer; and
(iii) combining melted solubilizer with melted surfactant to form a melted vehicle.

As described above, the melting of step (a) can be performed using standard heating techniques in the art. This also applies to steps (i) and (ii). In some embodiments, the heating temperatures of steps (i) and (ii) are the same. In some embodiments, the heating temperatures of steps (i) and (ii) are different.

In some embodiments, the at least one non-ionic surfactant having an HLB value of at least 10 in step (i) is heated to about 40, 45, 50, 55, 60, 65, 70, 75, 80, 85, 90 or more degrees C. In some embodiments, the at least one non-ionic surfactant having an HLB value of at least 10 in step (i) is heated to about 50° to 85° C. In some embodiments, the at least one non-ionic surfactant having an HLB value of at least 10 in step (i) is heated to about 50° to 70° C. In some embodiments, the at least one non-ionic surfactant having an HLB value of at least 10 in step (i) is heated to about 50° C. In some embodiments, the at least one non-ionic surfactant having an HLB value of at least 10 in step (i) is heated to about 60° C. In some embodiments, the at least one non-ionic surfactant having an HLB value of at least 10 in step (i) is heated to about 70° C. In some embodiments, the at least one non-ionic surfactant having an HLB value of at least 10 in step (i) is heated to about 80° C.

In some embodiments, the at least one water-soluble solubilizer in step (ii) is heated to about 40, 45, 50, 55, 60, 65, 70, 75, 80, 85, 90 or more degrees C. In some embodiments, the at least one water-soluble solubilizer in step (ii) is heated to about 50° to 90° C. In some embodiments, the at least one water-soluble solubilizer in step (ii) is heated to about 80° to 85° C. In some embodiments, the at least one water-soluble solubilizer in step (ii) is heated to about 50° C. In some embodiments, the at least one water-soluble solubilizer in step (ii) is heated to about 60° C. In some embodiments, the at least one water-soluble solubilizer in step (ii) is heated to about 70° C. In some embodiments, the at least one water-soluble solubilizer in step (ii) is heated to about 80° C.

In some embodiments, the at least one non-ionic surfactant having an HLB value of at least 10 in step (i) is heated to about 50 to 70° C., and the at least one water-soluble solubilizer in step (ii) is heated to about 80 to 85° C. In some embodiments, the at least one non-ionic surfactant having an HLB value of at least 10 in step (i) is heated to about 60° C., and the at least one water-soluble solubilizer in step (ii) is heated to about 80° C.

After performing steps (i) and (ii), the melted solubilizer may have the temperature adjusted to a temperature within the tolerances of the capsule shell. For example, the temperature tolerance of a gelatin capsule shell is about 65° C. Difference capsule shells can tolerate different temperatures, a person of skill in the art would readily identify appropriate temperatures based on the capsule shell being used.

When contacting the melted solubilizer and the melted surfactant, agitation is generally applied to ensure mixing of the melted surfactant and melted solubilizer. Typically, stirring is employed. The time of agitation/stirring will vary depending on the components of the melted surfactant and melted solubilizer, the size of the preparation, and the heating temperatures used. In some embodiments, stirring is performed for 0.25, 0.5, 0.75, 1, 2 or more hours. Agitation may be performed under vacuum during this step to dearate the solution.

Returning to step (b), when contacting the melted vehicle with Avacopan in step (b), the drug is dissolved in the heated vehicle. Dissolution of Avacopan can be achieved by a number of techniques including waiting an appropriate amount of time or agitating the solution to increase the rate of dissolution. In some embodiments, the heated vehicle with Avacopan in step (b) is agitated by stirring. Stirring times can be between one to six or more hours. In some embodiments, the stirring time is for 1, 2, 3, 4, 5 6 or more hours. In some embodiments, the stirring time is for about 3.5 hours.

Encapsulation of the drug solution is performed using known techniques in the art. One such machine useful for encapsulating is a Shionogi F40 filler. A person of skill in the art will be aware of additional equivalent machines.

There are a number of means known in the art for cooling a desired substance. The cooling in recited step (d) can include passive activities such as allowing the encapsulated drug solution to equilibrate to room temperature or more active steps such as placing the encapsulated drug solution in a refrigerated area to increase the rate of cooling.

A person of skill in the art will recognize the each of the above steps does not need to be performed in the recited order to prepare a solid solution capsule comprising Avacopan. For example, after dissolution of Avacopan in the heated vehicle (step (b)), to form a drug mixture, the drug mixture can be cooled to form a solid solution. As discussed above, cooling can include passive activities such as allowing the encapsulated drug solution to equilibrate to room temperature or more active steps such as placing the encapsulated drug solution in a refrigerated area to increase the rate of cooling.

In some embodiments, the total weight of the vehicle comprises a 30:70 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 30:70 and 65:35. In some embodiments, wherein the total weight of the vehicle comprises a 35:65 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 35:65 to 65:35. In some embodiments, the total weight of the vehicle comprises a 45:55 to 55:45 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 45:55 to 55:45. In some embodiments, the total weight of the vehicle comprises about a 50:50 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 50:50. In some embodiments, the total weight of the vehicle comprises about a 40:60 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 40:60. In some embodiments, the total weight of the vehicle comprises about a 30:70 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 30:70.

IV. Examples

The following examples are offered to illustrate, but not to limit, the claimed invention.

Example 1—Phase 2 Clinical Study

The study is a randomized, double-blind, placebo-controlled, three group Phase 2 trial in approximately 390 subjects with moderate to severe hidradenitis suppurativa (Hurley stage II or III). Subjects will be randomized 1:1:1 to a treatment of 10 mg Avacopan twice daily, 30 mg Avacopan twice daily or placebo for 12 weeks. Other systemic treatments for HS including anti-TNF-α treatments are prohibited. Stable antibiotic therapy with doxycycline or minocycline is allowed as specified in the protocol. Subjects treated with 10 mg or 30 mg twice daily during the blinded, placebo-controlled 12-week treatment period will be followed by an additional 24-week, active treatment period during which they will continue to receive the same dose regimen, either 10 mg or 30 mg Avacopan twice daily. Subjects on placebo who complete the blinded, placebo-controlled 12-week period will be re-randomized 1:1 to receive 10 mg or 30 mg Avacopan twice daily during the 24-week active treatment period. During the 24-week active treatment period the treatment assignment to 10 mg or 30 mg twice daily will not be disclosed to the patient, study personnel at the site or the sponsor. Thereafter, all subjects will be followed without study drug for 8 weeks before they exit the study.

Study Interventions/Methodology

Eligible adult subjects (at least 18 years of age) with moderate to severe hidradenitis suppurativa (Hurley stage II or III) as specified by the eligibility criteria are allowed to enter the study.

Subjects will be randomized 1:1:1 to receive 10 mg Avacopan twice daily, 30 mg Avacopan twice daily or matching placebo for 12 weeks in a double-blind, placebo-controlled manner.

To obtain balance across treatment groups, a stratified randomization scheme will be implemented. The stratification factors and strata within each factor are listed below. Eligible subjects will be randomized with equal chance (i.e. 1:1:1) to one of the three treatment groups within each stratum based on a non-dynamic, list-based blocked randomization scheme.

1. Hurley stage (Stage II vs III):
   a. Stage II disease: one or more widely separated recurrent abscesses with tract formation and scars, or
   b. Stage III disease: multiple interconnected tracts and abscesses across an entire area, with diffuse or near diffuse involvement.
2. Concomitant antibiotic therapy (Yes vs No)
   a. Concomitantly treated with doxycycline or minocycline as the only allowed antibiotic treatment for HS, or
   b. No concomitant antibiotic therapy.
3. Anti-TNF-α treatment (Treatment naïve vs Previous treatment):
   a. Did not previously receive anti-TNF-α drug such as adalimumab or infliximab (anti-TNF-α drug naïve), or
   b. Previously (but no longer) received an anti-TNF-α drug and
      completed anti-TNF-α treatment but may have relapsed, or
      was intolerant to anti-TNF-α treatment, or
      previously failed to respond or inadequately responded to anti-TNF-α treatment.

Not more than 20% of subjects will be in stratum 2a.

Eligible subjects will be randomized with equal chance (i.e. 1:1:1) to one of the three treatment groups within each stratum based on a non-dynamic, list-based blocked randomization scheme.
1) Placebo twice daily
2) Avacopan 10 mg twice daily
3) Avacopan 30 mg twice daily Subjects will be screened for eligibility based on the stage of the disease and their health status. The screening period will be up to 28 days. The primary efficacy analysis will occur when the last enrolled subject has completed the Week 12 visit. After the blinded 12-week treatment period, all subjects will continue an additional 24-week treatment with either 10 mg or 30 mg Avacopan twice daily. The treatment assignment to 10 mg or 30 mg twice daily will not be disclosed to the patient, study personnel at the site or the sponsor. Thereafter, all subjects will be followed for 8 weeks.

All subjects will visit the study center during the 28-day screening period, and, if eligible, on Day 1 and Weeks 2, 4, 8, 12, 16, 20, 24, 28, 32, 36, and 44 of the study. Study drug will be dispensed at the study site and subjects will take the first dose of study drug, i.e., Avacopan or matching placebo, while at the study center. Following the first dose, subjects will take study drug twice daily which will continue for 12 weeks (84 days). Thereafter, all subjects will take Avacopan study drug for 24 weeks (168 days), after which all subjects will be followed for 8 weeks (56 days) without taking study medication.

Subjects will be discontinued from the study when all the Study Week 44 visit procedures have been completed.

Subjects who experience a flare of HS during the study will be treated by the Investigator which may include a maximum 1-week course of antibiotic rescue treatment with doxycycline or minocycline or intralesional Kenalog® rescue injections (triamcinolone acetonide, 10 mg total maximum per subject within a period no longer than 1 week). These subjects will be requested to remain in the study and to complete all study procedures if possible. During this time, subjects may continue to receive the study drug as instructed, if assessed as clinically feasible by the investigator.

Study Drug, Dose, and Mode of Administration

Study subjects will receive active Avacopan or placebo capsules as study drug. The study drug consists of hard gelatin capsules containing 10 mg Avacopan or placebo administered orally. Avacopan and placebo bottles and capsules will be identical in appearance.

Subjects will be asked to take 3 capsules of study drug orally with water and preferably with food every morning, and 3 capsules with water and preferably with food in the evening approximately 12 hours after the morning dose, as instructed. Study drug will be taken for 36 weeks (252 days) continuously.

A Scheme of the Study is shown in FIG. 1.

Primary Objectives

The primary objectives of this clinical trial include:
1. Evaluation of the efficacy of Avacopan compared to placebo in subjects with Hurley Stage II or III hidradenitis suppurativa (HS) based on subjects achieving a Hidradenitis Suppurativa Clinical Response (HiSCR) after 12 weeks of treatment. HiSCR is defined as at least a 50% reduction in abscess and inflammatory nodule (AN) count with no increase in abscess count and no increase in draining fistula count at Week 12 relative to baseline.
2. Evaluation of the safety of Avacopan compared to placebo in these subjects based on the adverse event incidence, changes from baseline in laboratory parameters, and vital signs Secondary Objectives The secondary objectives of this study include:
1. Evaluation of the efficacy of Avacopan compared to placebo in these subjects include:
    a. HiSCR: proportion of subjects achieving HiSCR by each timepoint,
    b. The subject's global assessment of skin pain numeric rating scale (NRS),
    c. The modified Sartorius score, and
    d. Achieving an AN count of 0, 1, or 2
2. Assessment of subject reported outcomes including health-related quality-of-life changes based on the Short Form-36 version 2 (SF-36 v2), the EuroQOL-5D-5L (EQ-5D-5L), Hidradenitis Suppurativa Quality of Life (HiSQOL) Index, the Dermatology Life Quality Index (DLQI), and the Work Productivity and Activity Impairment Questionnaire: Specific Health Problem (WPAI: SHP) with Avacopan compared to placebo.
3. Evaluation of the pharmacokinetic profile of Avacopan in subjects with HS.
4. Evaluation of the safety and efficacy of Avacopan treatment from Day 1 by each timepoint up to Week 44 in subjects with HS.
5. Evaluation of the efficacy of avacopan compared to placebo in these subjects include:
    a. The Sartorius score, International HS Severity Scoring System (IHS4) score, HS Physician Global Assessment (HS-PGA),
    b. Proportion of subjects who experienced flare, who experienced loss of response during Period 2, who received oral antibiotic rescue therapy or lesion intervention, and who received disallowed opioid pain therapy, and
    c. The duration of flare in days.
6. Evaluation of health-economic information.

Study Treatments

Treatments for each group are shown in Table 1.

The treatment period is 36 weeks (252 days), followed by an 8-week (56 days) follow-up period without taking study medication. Subjects will be randomized 1:1:1 to receive placebo, 10 mg Avacopan or 30 mg Avacopan b.i.d. for the blinded, placebo-controlled treatment for the first 12 weeks. Subjects randomized to 10 mg and 30 mg Avacopan will continue with the same drug regimen during the next 24 week active drug treatment period. Subjects randomized to placebo during the first 12-week period will be re-randomized to receive either 10 mg or 30 mg Avacopan b.i.d. during the 24-week active drug treatment period. Study treatment-group specific drug kits will be dispensed at relevant study visits

TABLE 1

Avacopan/Placebo Treatment for the Two Study Groups

| | 12-Week Placebo-Controlled Treatment | 24-Week Active Drug Treatment |
|---|---|---|
| Group A Placebo | Kit # 1 | Re-randomized 50% to Kit # 2 50% to Kit # 3 |
| Group B 10 mg Avacopan | Kit # 2 | Kit # 2 |
| Group C 30 mg Avacopan | Kit # 3 | Kit # 3 |

Study Flow

Subjects will be screened for eligibility based on the stage of the disease and their health status. The screening period will be up to 28 days. The primary efficacy analysis can occur when the last enrolled subject has completed the Week 12 visit. After the blinded, placebo-controlled 12-week treatment period, all subjects will continue with a 24-week active treatment with 10 mg Avacopan twice daily or 30 mg Avacopan twice daily. After Week 36, all subjects will be followed for 8 weeks without receiving study medication.

All subjects will visit the study center during the 28-day screening period, and, if eligible, on Day 1 and Weeks 2, 4, 8, 12, 16, 20, 24, 28, 32, 36, and 44 of the study. Study drug will be dispensed at the study site and subjects will take the first dose of study drug, i.e. Avacopan or matching placebo, while at the study center. Preferably, on visit days subjects should take their dose while on-site. Following the first dose, subjects will take study drug twice daily, which will continue for 12 weeks (84 days). Thereafter, all subjects will take Avacopan study drug for 24 weeks (168 days), after which they will be followed for 8 weeks (56 days) without taking study drug.

Subjects will exit the study when all the Study Week 44 visit procedures have been completed.

Subjects who experience a flare of HS during the study will be treated by the Investigator, which may include a maximum 1-week course of antibiotic rescue treatment with doxycycline or minocycline or intralesional Kenalog® rescue injections (triamcinolone acetonide, 10 mg total maximum per subject within a period no longer than 1 week). These subjects will be requested to remain in the study and to complete all study procedures if possible. During this time, subjects may continue to receive the study drug, if deemed clinically feasible by the investigator.

Product Characteristics

The study drug consists of hard gelatin capsules containing 10 mg Avacopan or placebo administered orally. Avacopan and placebo bottles and capsules will be identical in appearance. The capsules are manufactured under current good manufacturing practice.

Doses and Regimens

Subjects will be asked to take 3 capsules of study drug orally with water and preferably with food every morning, and 3 capsules with water and preferably with food in the evening approximately 12 hours after the morning dose, as instructed. Study drug will be taken for 36 weeks (252 days) continuously.

Subjects will be asked to bring all bottles of study drug, whether empty or not, to the study center at each study visit for study drug accountability.

If a subject misses a dose, the missed dose should be taken as soon as possible. If it is close to the time for their next dose (within 3 hours), the missed dose should not be taken and the next dose should be taken at the regular time.

On study visit days it is preferable that the subjects take the morning dose of study drug at the site following the collection of PK samples, if applicable to that visit.

Study Procedures

Study Day 1

If eligible for the study, the subject will visit the study center on Day 1. The following procedures will be performed before taking the first dose of study drug:
  Stratification and randomization in the IRT system;
  A physical examination including body weight;
  Vital signs (temperature, sitting blood pressure, heart rate) after at least 3 minutes of rest;
  Blood samples will be collected for serum chemistry, hematology, and serum pregnancy test (in women of childbearing potential);
  A urine sample will be collected for urinalysis;
  The anatomic location and number of HS inflammatory nodules, abscesses, fistulae, and scars and the Hurley stage of HS will be recorded;
  Compliance with daily recording of skin pain in diaries will be checked and corrective action taken, if necessary;
  Items for the modified Sartorius score will be collected;
  IHS4 score will be calculated;
  Subjects will be asked to complete the SF-36 v2, EQ-5D-5L, and HiSQOL Index forms;
  The investigator will complete the HS-PGA;
  Compliance with daily recording of skin pain in daily diary starting 1 week prior to Day 1 will be checked and retraining provided, if necessary;
  Any pre-treatment adverse events (from time of the screening visit) will be recorded;
Thereafter, the following procedures will be performed:
  Study drug will be provided to the subject with dosing instructions;
  The subject will be asked to take the first dose of study drug while at the study center;
  The time of the dosing of study drug will be recorded;
  Any changes in concomitant medication use will be recorded, including alcohol intake, recreational drug use, non-prescription medications, herbal preparations or special diets;
  Any post-dosing adverse events will be recorded;
  After all study procedures have been completed, the subject will be reminded to:
    Record severity of skin pain and study drug dosing in daily diary;
    Come to the study center for the Week 2 study visit;
    Store the study drug in a cool and dry place according to label instructions for the duration of the study;
    Take the study drug, as instructed. On study visit days, it is preferable that the subjects take the morning dose of study drug at the site following the collection of PK samples, if applicable to that visit, and
    Continue taking all their other concomitant medications as usual.

Study Week 2 (Day 15)

The Study Week 2 visit must occur within ±2 days of the scheduled date. During this visit, the following study procedures will be performed:
  A physical examination including body weight;
  Vital signs (temperature, sitting blood pressure, heart rate) after at least 3 minutes of rest;
  Blood samples will be collected for shipment to the central laboratory for serum chemistry, hematology, and PK measurements; the date and time of collection of the PK sample will be recorded;
  The anatomic location and number of HS inflammatory nodules, abscesses, fistulae, and scars will be recorded;
  Compliance with daily recording of skin pain and drug dosing in diaries will be checked and re-training provided if necessary;
  Items for the modified Sartorius score will be collected;
  IHS4 score will be calculated;
  The investigator will complete the HS-PGA;
  The date and time of the last dose of study drug prior to collection of the PK sample will be recorded;

If the subject has not yet taken the morning dose of study drug for this day, the subject will be asked to take the dose;

The bottle of study drug will be checked to make sure the subject is taking the study drug as instructed;

Any changes in concomitant medication use will be recorded, including alcohol intake, recreational drug use, non-prescription medications, herbal preparations or special diets;

Any adverse events will be recorded;

After all study procedures have been completed, the subject will be reminded to:
  Record severity of skin pain and study drug dosing in daily diary;
  Come to the study center for the Week 4 study visit;
  Store the study drug in a cool and dry place according to label instructions for the duration of the study;
  Take the study drug as instructed. On study visit days, it is preferable that the subjects take the morning dose of study drug at the site following the collection of PK samples, if applicable to that visit, and
  Continue taking all their other concomitant medications as usual.

Study Week 4 (Day 29)

The Study Week 4 visit must occur within ±2 days of the scheduled date. During this visit, the following study procedures will be performed:
  A physical examination including body weight;
  Vital signs (temperature, sitting blood pressure, heart rate) after at least 3 minutes of rest;
  Blood samples will be collected for serum chemistry, hematology, serum pregnancy test (in women of childbearing potential), and PK measurements; the date and time of collection of the PK sample will be recorded;
  The date and time of the last dose of study drug prior to collection of the PK sample will be recorded;
  If the subject has not yet taken the morning dose of study drug for this day, the subject will be asked to take the dose;
  A urine sample will be collected for urinalysis;
  The anatomic location and number of HS inflammatory nodules, abscesses, fistulae, and scars will be recorded;
  Compliance with daily recording of skin pain and study drug dosing in diaries will be checked and retraining provided, if necessary;
  Items for the modified Sartorius score will be collected;
  IHS4 score will be calculated;
  The investigator will complete the HS-PGA;
  Subjects will be asked to complete the SF-36 v2, EQ-5D-5L, and HiSQOL Index forms;
  Drug accountability will be performed on the returned bottle of study drug;
  Study drug will be dispensed;
  Any changes in concomitant medication use will be recorded, including alcohol intake, recreational drug use, non-prescription medications, herbal preparations or special diets;
  Any adverse events will be recorded;
  After all study procedures have been completed, the subject will be reminded to:
    Record severity of skin pain and study drug dosing in daily diary;
    Come to the study center for the Week 8 study visit;
    Store the study drug in a cool and dry place according to label instructions for the duration of the study;
    Take the study drug as instructed. On study visit days, it is preferable that the subjects take the morning dose of study drug at the site following the collection of PK samples, if applicable to that visit, and
    Continue taking all their other concomitant medications as usual.

Study Week 8 (Day 57)

The Study Week 8 visit must occur within ±2 days of the scheduled date. During this visit, the following study procedures will be performed:
  A physical examination including body weight;
  Vital signs (temperature, sitting blood pressure, heart rate) after at least 3 minutes of rest;
  Blood samples will be collected for serum chemistry, hematology, serum pregnancy test (in women of childbearing potential), and PK measurements; the date and time of collection of the PK sample will be recorded;
  The date and time of the last dose of study drug prior to collection of the PK sample will be recorded;
  If the subject has not yet taken the morning dose of study drug for this day, the subject will be asked to take the dose;
  A urine sample will be collected for urinalysis;
  The anatomic location and number of HS inflammatory nodules, abscesses, fistulae, and scars will be recorded;
  Compliance with daily recording of pain and study drug dosing in diaries will be checked and retraining provided, if necessary;
  Items for the modified Sartorius score will be collected;
  IHS4 score will be calculated;
  The investigator will complete the HS-PGA;
  Drug accountability will be performed, the bottle of study drug will be checked to make sure the subject is taking the study drug as instructed;
  Any changes in concomitant medication use will be recorded, including alcohol intake, recreational drug use, non-prescription medications, herbal preparations or special diets;
  Any adverse events will be recorded;
  After all study procedures have been completed, the subject will be reminded to:
    Record severity of skin pain and study drug administration in daily diary;
    Come to the study center for the Week 12 study visit;
    Store the study drug in a cool and dry place according to label instructions for the duration of the study;
    Take the study drug as instructed. On study visit days, it is preferable that the subjects take the morning dose of study drug at the site following the collection of PK samples, if applicable to that visit, and
    Continue taking all their other concomitant medications as usual.

Study Week 12 (Day 85)

The Study Week 12 visit must occur within ±2 days of the scheduled date. During this visit, the following study procedures will be performed:
  A physical examination including body weight;
  Vital signs (temperature, sitting blood pressure, heart rate) after at least 3 minutes of rest;
  Blood samples will be collected for serum chemistry, hematology, serum pregnancy test (in women of childbearing potential), and PK measurements; the date and time of collection of the PK sample will be recorded;
  The date and time of the last dose of study drug prior to collection of the PK sample will be recorded;
  If the subject has not yet taken the morning dose of study drug for this day, the subject will be asked to take the dose;

A urine sample will be collected for urinalysis;
The anatomic location and number of HS inflammatory nodules, abscesses, fistulae, and scars will be recorded;
Compliance with daily recording of pain in diaries will be checked and re-training provided, if necessary;
Items for the modified Sartorius score will be collected;
The investigator will complete the HS-PGA;
IHS4 score will be calculated;
Subjects will be asked to complete the SF-36 v2, EQ-5D-5L, and HiSQOL Index forms;
Drug accountability will be performed on the returned bottle of study drug;
Study drug will be dispensed; Note: At this visit, subjects who were assigned to placebo arm will be re-randomized to receive 10 mg or 30 mg Avacopan twice a day;
Any changes in concomitant medication use will be recorded, including alcohol intake, recreational drug use, non-prescription medications, herbal preparations or special diets;
Any adverse events will be recorded;
After all study procedures have been completed, the subject will be reminded to:
Record severity of skin pain and study drug dosing in daily diary;
Come to the study center for the Week 16 study visit;
Store the study drug in a cool and dry place according to label instructions for the duration of the study;
Take the study drug as instructed. On study visit days, it is preferable that the subjects take the morning dose of study drug at the site following the collection of PK samples, if applicable to that visit, and
Continue taking all their other concomitant medications as usual.

Study Week 16 (Day 113)
The Study Week 16 visit must occur within ±2 days of the scheduled date. During this visit, the following study procedures will be performed:
A physical examination including body weight;
Vital signs (temperature, sitting blood pressure, heart rate) after at least 3 minutes of rest;
Blood samples will be collected for serum chemistry, hematology, serum pregnancy test (in women of childbearing potential), and PK measurements; the date and time of collection of the PK sample will be recorded;
The date and time of the last dose of study drug prior to collection of the PK sample will be recorded;
If the subject has not yet taken the morning dose of study drug for this day, the subject will be asked to take the dose;
A urine sample will be collected for urinalysis;
The anatomic location and number of HS inflammatory nodules, abscesses, fistulae, and scars will be recorded;
Compliance with daily recording of pain and study drug dosing in diaries will be checked and re-training provided, if necessary;
Items for the modified Sartorius score will be collected;
IHS4 score will be calculated;
The investigator will complete the HS-PGA;
Subjects will be asked to complete the SF-36 v2, EQ-5D-5L, and HiSQOL Index forms;
Drug accountability will be performed, the bottle of study drug will be checked to make sure the subject is taking the study drug as instructed;
Any changes in concomitant medication use will be recorded, including alcohol intake, recreational drug use, non-prescription medications, herbal preparations or special diets;
Any adverse events will be recorded;
After all study procedures have been completed, the subject will be reminded to:
Record severity of skin pain and study drug dosing in daily diary;
Come to the study center for the Week 20 study visit;
Store the study drug in a cool and dry place according to label instructions for the duration of the study;
Take the study drug as instructed. On study visit days, it is preferable that the subjects take the morning dose of study drug at the site following the collection of PK samples, if applicable to that visit, and
Continue taking all their other concomitant medications as usual.

Study Week 20 (Day 141)
The Study Week 20 visit must occur within ±2 days of the scheduled date. During this visit, the following study procedures will be performed:
A physical examination including body weight;
Vital signs (temperature, sitting blood pressure, heart rate) after at least 3 minutes of rest;
Blood samples will be collected for serum chemistry, hematology, serum pregnancy test (in women of childbearing potential), and PK measurements; the date and time of collection of the PK sample will be recorded;
The date and time of the last dose of study drug prior to collection of the PK sample will be recorded;
If the subject has not yet taken the morning dose of study drug for this day, the subject will be asked to take the dose;
A urine sample will be collected for urinalysis;
The anatomic location and number of HS inflammatory nodules, abscesses, fistulae, and scars will be recorded;
Compliance with daily recording of pain in diaries will be checked and re-training provided, if necessary;
Items for the modified Sartorius score will be collected;
IHS4 score will be calculated;
The investigator will complete the HS-PGA;
Drug accountability will be performed on the returned bottle of study drug;
Study drug will be dispensed;
Any changes in concomitant medication use will be recorded, including alcohol intake, recreational drug use, non-prescription medications, herbal preparations or special diets;
Any adverse events will be recorded;
After all study procedures have been completed, the subject will be reminded to:
Record severity of skin pain and study drug dosing in daily diary;
Come to the study center for the Week 24 study visit;
Store the study drug in a cool and dry place according to label instructions for the duration of the study;
Take the study drug as instructed. On study visit days, it is preferable that the subjects take the morning dose of study drug at the site following the collection of PK samples, if applicable to that visit, and
Continue taking all their other concomitant medications as usual.

Study Week 24 (Day 169)
The Study Week 24 visit must occur within ±2 days of the scheduled date. During this visit, the following study procedures will be performed:
Blood samples will be collected for serum chemistry, hematology, serum pregnancy test (in women of childbearing potential), and PK measurements; the date and time of collection of the PK sample will be recorded;

Drug accountability will be performed, the bottle of study drug will be checked to make sure the subject is taking the study drug as instructed;

Any changes in concomitant medication use will be recorded, including alcohol intake, recreational drug use, non-prescription medications, herbal preparations or special diets;

Any adverse events will be recorded;

After all study procedures have been completed, the subject will be reminded to:
  Record severity of skin pain and study drug dosing in daily diary;
  Come to the study center for the Week 28 study visit;
  Store the study drug in a cool and dry place according to label instructions for the duration of the study;
  Take the study drug as instructed. On study visit days, it is preferable that the subjects take the morning dose of study drug at the site following the collection of PK samples, if applicable to that visit, and
  Continue taking all other concomitant medications as usual.

Study Week 28 (Day 197)

The Study Week 28 visit must occur within ±2 days of the scheduled date. During this visit, the following study procedures will be performed:
  A physical examination including body weight;
  Vital signs (temperature, sitting blood pressure, heart rate) after at least 3 minutes of rest;
  Blood samples will be collected for serum chemistry, hematology, serum pregnancy test (in women of childbearing potential), and PK measurements; the date and time of collection of the PK sample will be recorded;
  The date and time of the last dose of study drug prior to collection of the PK sample will be recorded;
  If the subject has not yet taken the morning dose of study drug for this day, the subject will be asked to take the dose;
  A urine sample will be collected for urinalysis;
  The anatomic location and number of HS inflammatory nodules, abscesses, fistulae, and scars will be recorded;
  Compliance with daily recording of pain and study drug dosing in diaries will be checked and re-training provided, if necessary;
  Items for the modified Sartorius score will be collected;
  IHS4 score will be calculated;
  The investigator will complete the HS-PGA;
  Drug accountability will be performed on the returned bottle of study drug;
  Study drug will be dispensed;
  Any changes in concomitant medication use will be recorded, including alcohol intake, recreational drug use, non-prescription medications, herbal preparations or special diets;
  Any adverse events will be recorded;
  After all study procedures have been completed, the subject will be reminded to:
    Record severity of skin pain and study drug dosing in daily diary;
    Come to the study center for the Week 32 study visit;
    Store the study drug in a cool and dry place according to label instructions for the duration of the study;
    Take the study drug as instructed. On study visit days, it is preferable that the subjects take the morning dose of study drug at the site following the collection of PK samples, if applicable to that visit, and
    Continue taking all their other concomitant medications as usual.

Study Week 32 (Day 225)

The Study Week 32 visit must occur within ±2 days of the scheduled date. During this visit, the following study procedures will be performed:
  Blood samples will be collected for serum chemistry, hematology, serum pregnancy test (in women of childbearing potential), and PK measurements; the date and time of collection of the PK sample will be recorded;
  Drug accountability will be performed, the bottle of study drug will be checked to make sure the subject is taking the study drug as instructed;
  Any changes in concomitant medication use will be recorded, including alcohol intake, recreational drug use, non-prescription medications, herbal preparations or special diets;
  Any adverse events will be recorded;
  After all study procedures have been completed, the subject will be reminded to:
    Record severity of skin pain and study drug dosing in daily diary;
    Come to the study center for the Week 36 study visit;
    Store the study drug in a cool and dry place according to label instructions for the duration of the study;
    Take the study drug as instructed. On study visit days, it is preferable that the subjects take the morning dose of study drug at the site following the collection of PK samples, if applicable to that visit, and
    Continue taking all their other concomitant medications as usual.

Study Week 36 (Day 253)

The Study Week 36 visit must occur within ±2 days of the scheduled date. During this visit, the following study procedures will be performed:
  A physical examination including body weight;
  Vital signs (temperature, sitting blood pressure, heart rate) after at least 3 minutes of rest;
  Blood samples will be collected for serum chemistry, hematology, serum pregnancy test (in women of childbearing potential), and PK measurements; the date and time of collection of the PK sample will be recorded;
  The date and time of the last dose of study drug prior to collection of the PK sample will be recorded;
  A urine sample will be collected for urinalysis;
  The anatomic location and number of HS inflammatory nodules, abscesses, fistulae, and scars will be recorded;
  Compliance with daily recording of pain and study drug dosing in diaries will be checked and re-training provided, if necessary;
  Items for the modified Sartorius score will be collected;
  IHS4 score will be calculated;
  The investigator will complete the HS-PGA;
  Subjects will be asked to complete the SF-36 v2, EQ-5D-5L, and HiSQOL Index forms;
  Drug accountability will be performed on the returned bottle(s) of study drug;
  Any changes in concomitant medication use will be recorded, including alcohol intake, recreational drug use, non-prescription medications, herbal preparations or special diets;
  Any adverse events will be recorded;
  After all study procedures have been completed, the subject will be reminded to:
    Record severity of skin pain in daily diary;
    Come to the study center for the Week 44 study visit, and
    Continue taking all their other concomitant medications as usual.

Study Week 44 (Day 309)

The Study Week 44 (follow-up) visit must occur within ±4 days of the scheduled date. During this visit, the following study procedures will be performed:

- A physical examination including body weight;
- Vital signs (temperature, sitting blood pressure, heart rate) after at least 3 minutes of rest;
- Blood samples will be collected for serum chemistry, hematology, and PK measurements; the date and time of collection of the PK sample will be recorded;
- A urine sample will be collected for urinalysis;
- The anatomic location and number of HS inflammatory nodules, abscesses, fistulae, and scars will be recorded;
- Items for the modified Sartorius score will be collected;
- IHS4 score will be calculated;
- The investigator will complete the HS-PGA;
- Subjects will be asked to complete the SF-36 v2, EQ-5D-5L, and HiSQOL Index forms;
- The completed daily diary will be collected;
- Any changes in concomitant medication use will be recorded, including alcohol intake, recreational drug use, non-prescription medications, herbal preparations or special diets;
- Any adverse events will be recorded;
- After all study procedures have been completed, the subject will exit the study.

Early Termination Visit

If a subject will be withdrawn early from the study, the following termination procedures must be completed whenever possible:

- A physical examination including body weight;
- Vital signs (temperature, sitting blood pressure, heart rate) after at least 3 minutes of rest;
- Blood samples for serum chemistry, hematology, and serum pregnancy test (in women of childbearing potential), and PK measurements; the date and time of collection of the PK sample will be recorded;
- A urine sample will be collected for urinalysis;
- The anatomic location and number of HS inflammatory nodules, abscesses, fistulae, and scars will be recorded;
- Items for the modified Sartorius score will be collected if the prior visit where this assessment was made was more than 2 weeks before;
- Subjects will be asked to complete the SF-36 v2, EQ-5D-5L, and HiSQOL Index forms, if the prior visit where these assessments were made was more than 2 weeks before;
- The investigator will complete the HS-PGA, if the prior visit where these assessments were made was more than 2 weeks before;
- Drug accountability will be performed on the returned bottles of study drug;
- Completed daily diary will be collected;
- Any changes in concomitant medication use will be recorded, including alcohol intake, recreational drug use, non-prescription medications, herbal preparations or special diets;
- Any adverse events will be recorded.

Study Assessments

Location and Extent of Hidradenitis Suppurativa Assessment

The location and extent of HS will be assessed by recording the anatomic location(s) of the disease, as well as the number of HS inflammatory nodules, abscesses, fistulae, and scars in each of the locations in the EDC. All study investigators will receive and have passed a study specific training to assess HS lesions. The same investigator should assess the lesions at each visit to assure consistency. If this is not possible, a trained back-up investigator at the site should perform the evaluation.

The information regarding location and extent of HS involvement will be used to determine the Hurley stage and also to calculate the HiSCR at post baseline visits. The HiSCR will be calculated programmatically in the EDC.

Modified Sartorius Score

Twelve body areas will be evaluated to calculate the modified Sartorius score:

- left and right axillae,
- left and right inframammary areas,
- intermammary area,
- left and right buttocks,
- left and right inguino-crural folds,
- perianal area and perineal area, and
- other (specify).

A score of 4 indicates the least severe disease, and higher scores indicate increasingly severe disease. There is no upper limit in the score (Sartorius et al, 2003).

The presence of nodules, abscesses, fistulae, scars, and other findings will be recorded in the EDC. The longest distance between two lesions and whether lesions are separated by normal skin will also be recorded.

International Hidradenitis Suppurativa Severity Score System

The International Hidradenitis Suppurativa Severity Score (IHS4) is simple to calculate and validated with the use of existing physician-derived outcomes such as HS-PGA, Hurley classification, MSS or Expert Opinion classification) and patient-reported outcome measure (DLQI). IHS4 score (points)=(number of nodules multiplied by 1)+(number of abscesses multiplied by 2)+[number of draining tunnels (fistulae/sinuses) multiplied by 4]. A score of 3 or less signifies mild HS, a score of 4-10 signifies moderate HS and a score of 11 or higher signifies severe HS.

Hidradenitis Suppurativa-Physician's Global Assessment (HS-PGA)

The HS-PGA is an ordinal scale specific to HS that categorizes patients into clear, minimal, mild, moderate, severe, or very severe disease, and it was used successfully in a phase 2 interventional clinical trial. A recently developed six stage PGA was defined as follows (Kimball et al, 2012):

- Clear: no inflammatory or non-inflammatory nodules
- Minimal: Only the presence of non-inflammatory nodules
- Mild: Less than 5 inflammatory nodules or 1 abscess or draining fistula and no inflammatory nodules
- Moderate: Less than 5 inflammatory nodules or one abscess or draining fistula and one or more inflammatory nodules or 2-5 abscesses or draining fistulae and less than ten inflammatory nodules
- Severe: 2-5 abscesses or draining fistulae and ten or more inflammatory nodules
- Very severe: More than 5 abscesses or draining fistulae Global Skin Pain Subjects will record the maximum severity pain on a numeric rating scale from 0 (no skin pain) to 10 (skin pain as bad as can be imagined) in a daily diary from one week prior to Day 1 through the Week 44 visit.

The weekly average of the maximum severity pain will be calculated programmatically.

Health-Related Quality of Life Assessments

The SF-36 v2 and EQ-5D-5L instruments are widely accepted global non disease specific tools to measure changes in subjects' health-related quality of life. Forms for these instruments will be completed by study subjects to measure changes from baseline in health-related quality of life. Proven translations will be used for non-English speaking subjects, whenever possible.

The HiSQOL index has been developed as an HS-specific instrument to measure the impact of HS on subjects' quality of life.

Study personnel will facilitate completion of the quality of life questionnaires by the subjects, but will not complete the forms for the subjects. The administrator will establish a rapport with the subject, emphasize the importance of completing the form, and serve to answer questions and address concerns. The questionnaires should be completed by subjects before seeing the Investigator at the visit.

Pharmacokinetic Assessments & Analysis

Concentrations of Avacopan (and metabolites) will be determined. The date and time of the last dose of study drug prior to the sample collections must be recorded in the EDC system. The date and time of the PK sample collection must also be recorded.

Total plasma concentrations of Avacopan (and metabolites) will be determined using validated analytical methods.

Individual plasma concentrations of Avacopan and significant metabolites will be listed, plotted, and summarized descriptively and graphically. PK analysis may be performed in a subject subset only. The following parameters will be determined, where possible:

| | |
|---|---|
| $C_{max}$ | Maximum plasma concentration |
| $T_{max}$ | Time of maximum plasma concentration |
| $AUC_{0-6h}$ | Area under the plasma concentration-time curve from Time 0 to Hour 6 on Day 1 |
| $C_{min}$ | Trough level plasma concentrations at post-Day 1 visits |

The relationship between PK parameters (e.g., $C_{min}$) and efficacy endpoints such as HiSCR may also be evaluated.

Example 2—Summary of Top-Line Results from Phase II Trial

The Phase II AURORA clinical trial randomized 398 patients to one of three treatment arms. The study population included patients with moderate HS (Hurley Stage II) or severe HS (Hurley Stage III), which were stratified evenly across the treatment groups. The primary endpoint of the proportion of all patients (both moderate Hurley Stage II plus severe Hurley Stage III) achieving Hidradenitis Suppurativa Clinical Response (HiSCR), as assessed 10 mg twice-daily (BID) and 30 mg BID dosing regimens of avacopan against placebo after 12 weeks of treatment in the combined study population, was not achieved with statistical significance at either dose level, although a numerical improvement was noted at the 30 mg BID dose. Importantly, avacopan 30 mg BID demonstrated a statistically significant higher response than placebo in the pre-specified population of Hurley Stage III (severe) HS patients in the study. The Company plans to advance avacopan into Phase III development for the treatment of severe HS.

TABLE 2

Hidradenitis Suppurativa Clinical Response (HiSCR) Results

| | Placebo | Avacopan 10 mg BID | | (95% | Avacopan 30 mg BID | | (95% |
|---|---|---|---|---|---|---|---|
| | n/N (%) | n/N (%) | Δ % | CI) | n/N (%) | Δ % | CI) |
| All | 40/130 (30.8) | 30/134 (22.4) | −8.2 | (−18.7, 2.4) | 47/134 (35.1) | 4.4 | (−6.9, 15.5) |
| Hurley Stage II | 30/85 (35.3) | 18/84 (21.4) | −13.8 | (−26.8, −0.2) | 27/87 (31.0) | −4.3 | (−18.1, 9.6) |
| Hurley Stage III | 10/45 (22.2) | 12/50 (24.0) | 1.8 | (−15.3, 18.3) | 20/47 (42.6) | 20.3* | (1.6, 37.9) |

*p = 0.0349

A consistency of effect with avacopan was noted in Hurley Stage III patients across every secondary endpoint assessed to date. Favorable reductions for avacopan were observed in International HS Severity Score (IHS4), as well as reduction in AN (abscesses and inflammatory nodules), draining fistula, and abscess count at week 12 (all % change from baseline to week 12), relative to placebo.

Avacopan demonstrated a favorable safety profile. Treatment emergent adverse events (TEAEs) of all types were observed to be fewer in the avacopan groups (48.5%) than with placebo (55%). The majority of TEAEs were related to underlying HS and were mild to moderate. Serious TEAEs were observed in 2.3% of placebo patients vs. 1.5% on avacopan.

About Hidradenitis Suppurativa and the AURORA Trial

Hidradenitis Suppurativa (HS), also known as acne inversa, is a chronic disabling autoimmune skin disease characterized by recurrent, painful nodules, boils and abscesses.

The Phase II AURORA clinical trial randomized 398 patients with moderate-to-severe HS to one of three treatment arms. The primary endpoint assessed 10 mg BID and 30 mg BID dosing regimens of avacopan against placebo at 12 weeks of treatment, using the HiSCR scale. HiSCR response is defined as a ≥50% reduction in inflammatory lesion count (abscesses+inflammatory nodules), and no increase in abscesses or draining fistulas when compared with baseline. Secondary endpoints include percent improvement to week 12 between groups, the IHS4 (International Hidradenitis Suppurativa Severity Scoring System) reduction from baseline, and other validated secondary measurements.

Following the 12-week double-blind treatment period, the study will remain blinded. Patients on placebo were re-randomized to either the 10 mg BID or 30 mg avacopan BID dose group for an additional 24 weeks; patients treated with avacopan continued to receive the same dose (either 10 mg BID or 30 mg BID) for an additional 24 weeks. Patients will be followed for an additional 44 weeks for assessment of safety and efficacy.

Avacopan's selective inhibition of only the $C_5aR$ leaves the beneficial $C_5a$ pathway through the $C_5L2$ receptor functioning normally.

Example 3—Avacopan is Suprisingly Effective in Patients with Stage III HS

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating Hidradenitis Suppurativa (HS) in a subject in need thereof, said method comprising administering to said subject a compound of Formula I,

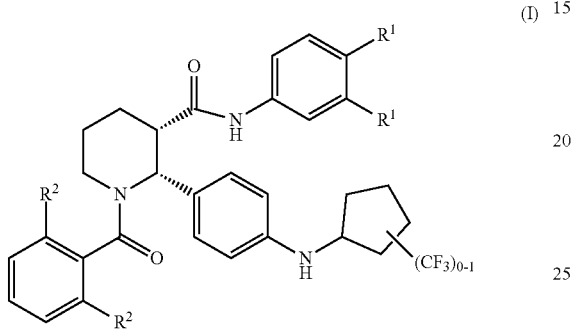

or a pharmaceutically acceptable salt thereof, wherein
said subject receives about 30 mg of the compound twice daily, wherein said subject has a Hurley score of Stage III, and wherein
each $R^1$ is independently selected from the group consisting of $CH_3$, $CF_3$, $CH_2CH_3$, Cl, 1-pyrrolidine, —O—$CH(CH_3)_2$, and $CH_2OH$; and
each $R^2$ is independently selected from the group consisting of $CH_3$ and F.

2. The method of claim 1, wherein the compound is selected from the group consisting of

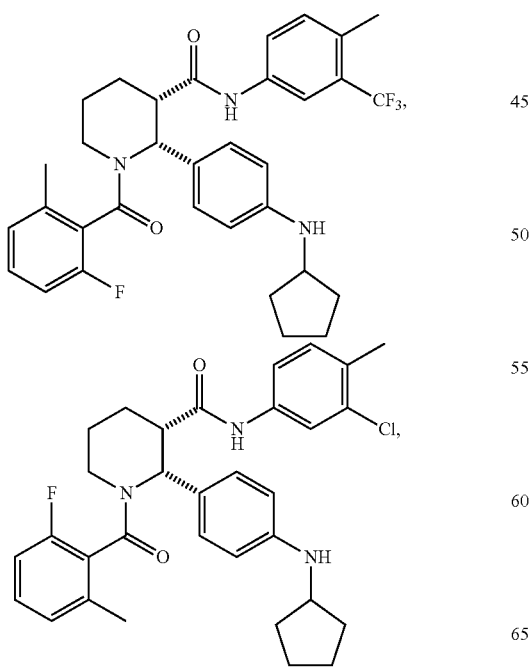

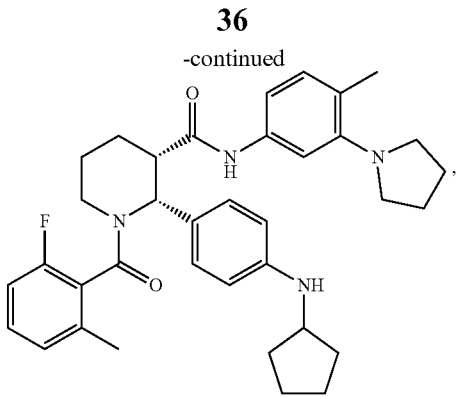

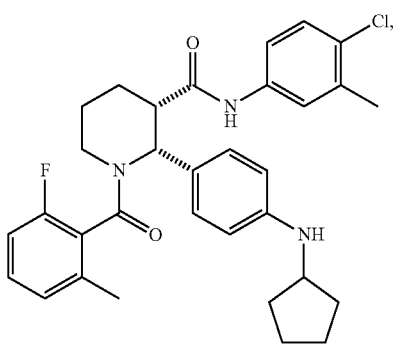

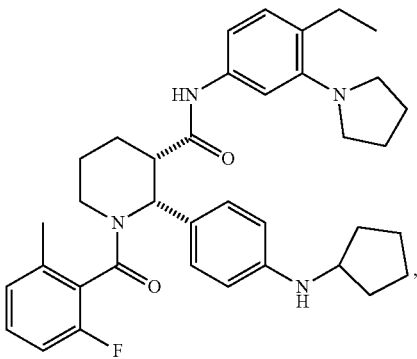

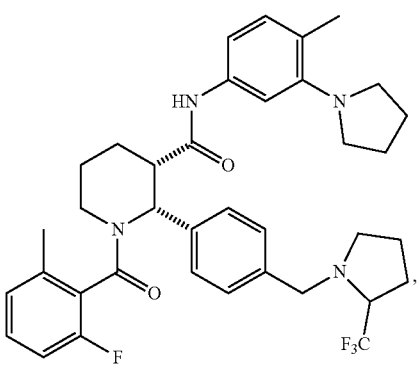

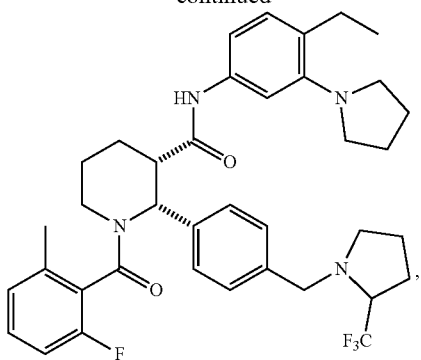
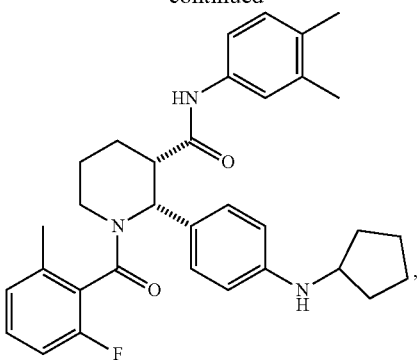
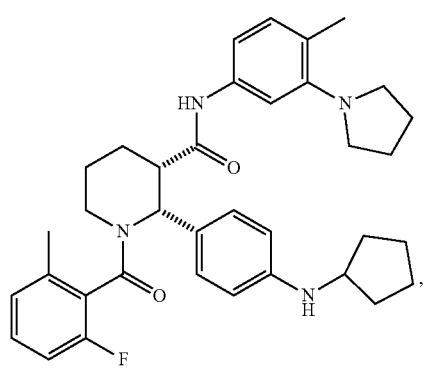
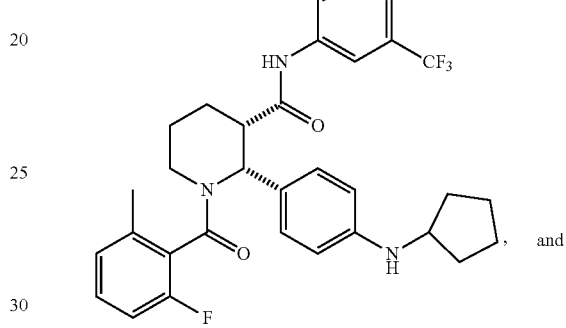
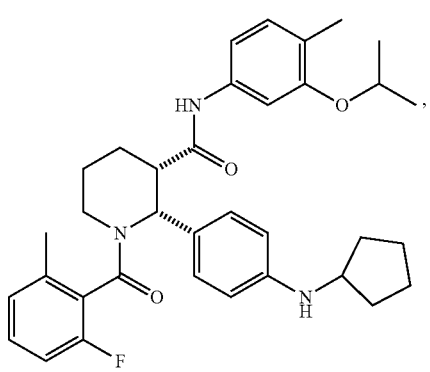
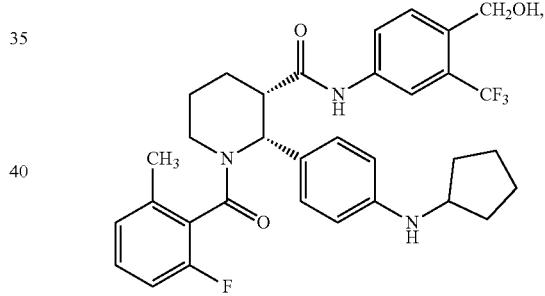
, and
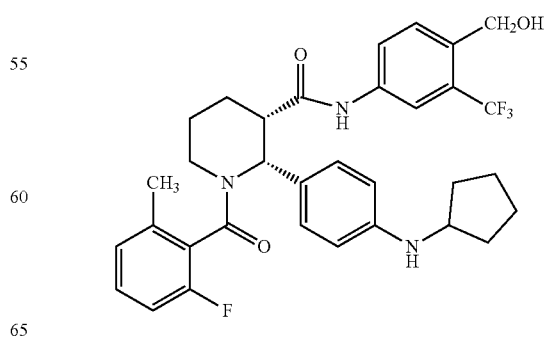
or a pharmaceutically acceptable salt thereof.
3. The method of claim 1, wherein the compound is
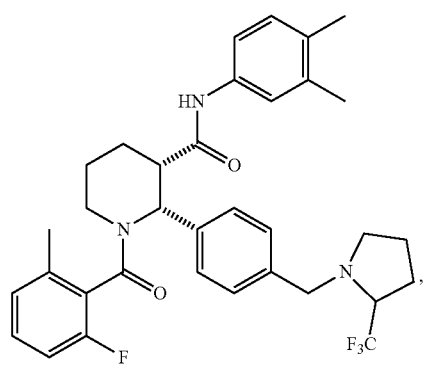
or a pharmaceutically acceptable salt thereof.

4. The method of claim 1, wherein the compound is Avacopan, having the formula

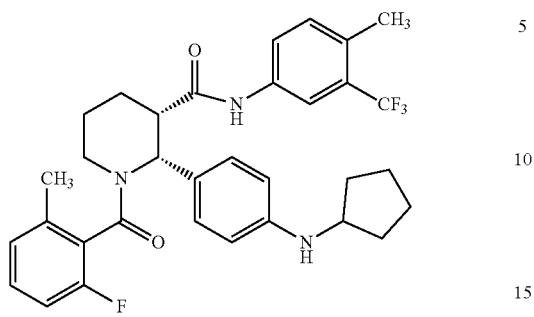

or a pharmaceutically acceptable salt thereof.

5. The method of claim 1, wherein the subject receives treatment for 12 weeks.

6. The method of claim 1, wherein the subject receives treatment for 26 weeks.

7. The method of claim 1, wherein the subject receives treatment for 52 weeks.

8. The method of claim 1, wherein the subject receives chronic treatment.

* * * * *